(12) United States Patent
Li et al.

(10) Patent No.: US 7,951,529 B2
(45) Date of Patent: May 31, 2011

(54) BIOMARKERS FOR BREAST CANCER

(75) Inventors: Jinong Li, Ellicott City, MD (US); Carolyn N. White, Baltimore, MD (US); Zhen Zhang, Dayton, MD (US); Daniel W. Chan, Clarksville, MD (US); Eric T. Fung, Los Altos, CA (US); Xiao-Ying Meng, Fremont, CA (US)

(73) Assignees: The Johns Hopkins University, Baltimore, MD (US); Vermillion, Inc., Austin, TX (US)

( * ) Notice: Subject to any disclaimer, the term of this patent is extended or adjusted under 35 U.S.C. 154(b) by 602 days.

(21) Appl. No.: 11/662,830

(22) PCT Filed: Sep. 16, 2005

(86) PCT No.: PCT/US2005/033168
§ 371 (c)(1),
(2), (4) Date: Mar. 4, 2008

(87) PCT Pub. No.: WO2006/034032
PCT Pub. Date: Mar. 30, 2006

(65) Prior Publication Data
US 2008/0311673 A1    Dec. 18, 2008

Related U.S. Application Data

(60) Provisional application No. 60/610,769, filed on Sep. 17, 2004.

(51) Int. Cl.
*C12Q 1/00*    (2006.01)

(52) U.S. Cl. ......................................................... 435/4
(58) Field of Classification Search ....................... 435/4
See application file for complete search history.

(56) References Cited

U.S. PATENT DOCUMENTS

| 5,833,989 | A | * | 11/1998 | Mossakowska et al. ... 424/185.1 |
| 6,294,349 | B1 | * | 9/2001 | Streckfus et al. ............ 435/7.23 |
| 2003/0096431 | A1 | | 5/2003 | Jackowski et al. |
| 2005/0059013 | A1 | | 3/2005 | Chan et al. |

FOREIGN PATENT DOCUMENTS

WO    WO 03076896 A2 *  9/2003

OTHER PUBLICATIONS

Colozza et al., Annals Oncol., 2005, 16:1723-1739.*
Coradini et al., Curr. Opin. Obst. Gyn. 2004, 16:49-55.*
Li et al., Clin. Chem., 2005, 51(12):2229-2235.*
Diamandis, Clin. Chem., 2006, 52(4):771.*
Merchant et al., Electrophoresis, 2000, 21: 1164-1177.*
Li, Jinong, et al., "Proteomics and Bioinformatics Approaches for Identification of Seruem Biomarkers to Detect Breast Cancer", Clinical Chemistry, vol. 48, No. 8, (2002), pp. 1296-1304.
Caputo, Emilia, et al., "Peptide profiling in epithelial tumor plasma by the emerging proteomic techniques", Journal of Chromotography B, vol. 819, (2005), pp. 59-66.

* cited by examiner

*Primary Examiner* — Hong Sang
(74) *Attorney, Agent, or Firm* — Edwards Angell Palmer & Dodge LLP; Peter F. Corless; Melissa Hunter-Ensor, Esq.

(57) ABSTRACT

The present invention provides protein-based biomarkers and biomarker combinations that are useful in qualifying breast cancer status in a patient. In particular, the biomarkers of this invention are useful to classify a subject sample as breast cancer or non-breast cancer. The biomarkers can be detected by SELDI mass spectrometry.

12 Claims, 23 Drawing Sheets

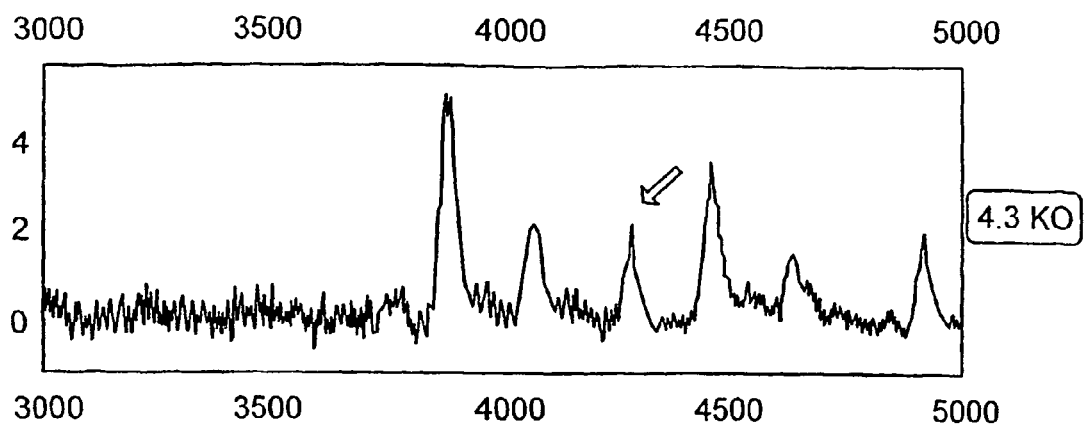
FIG. 1A (Marker I (Bc1))
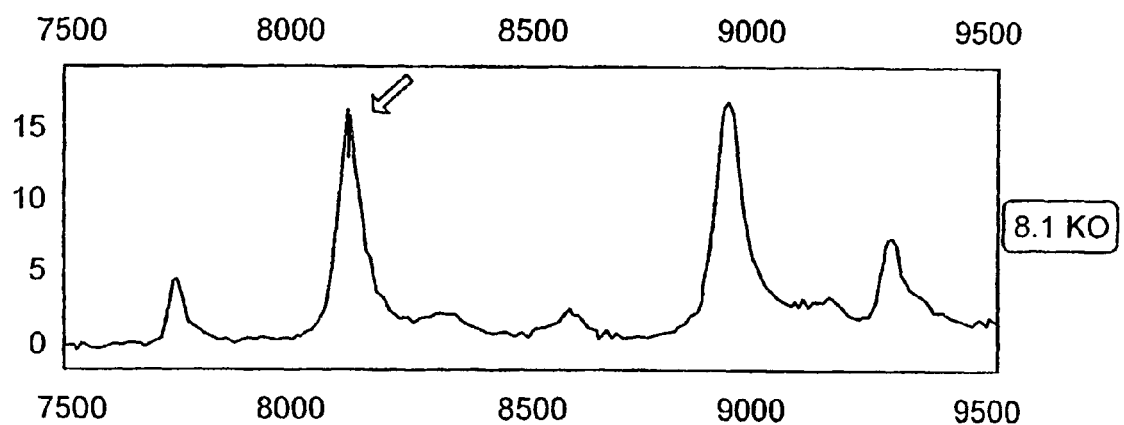
FIG. 1B (Marker II (Bc2))
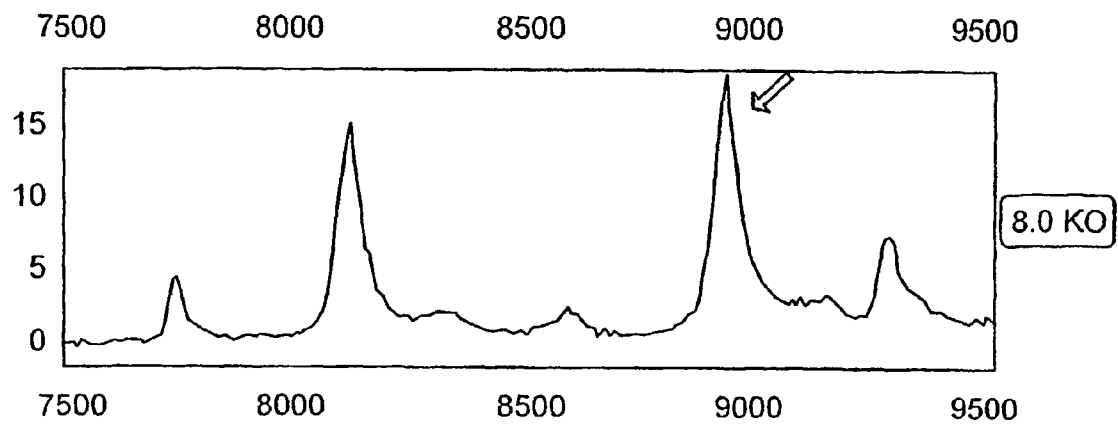
FIG. 1C (Marker III (BC3))

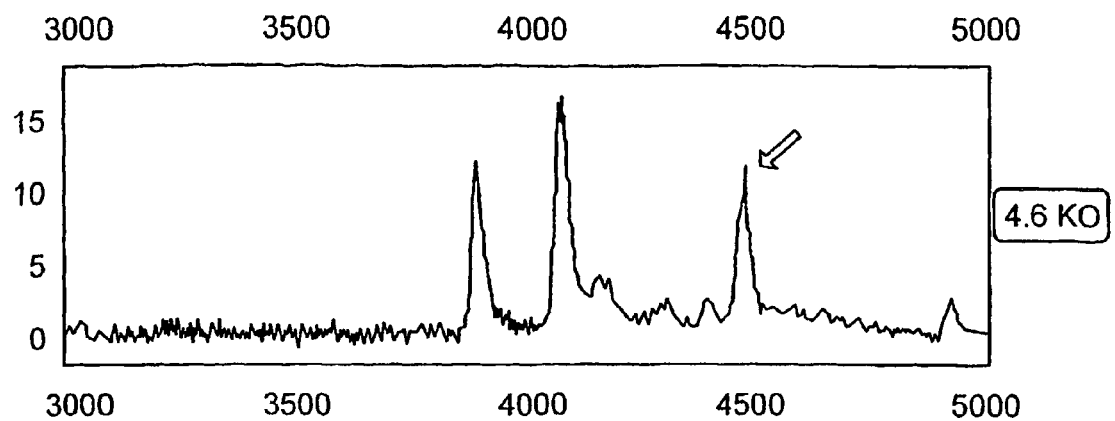
FIG. 1D (Marker IV)
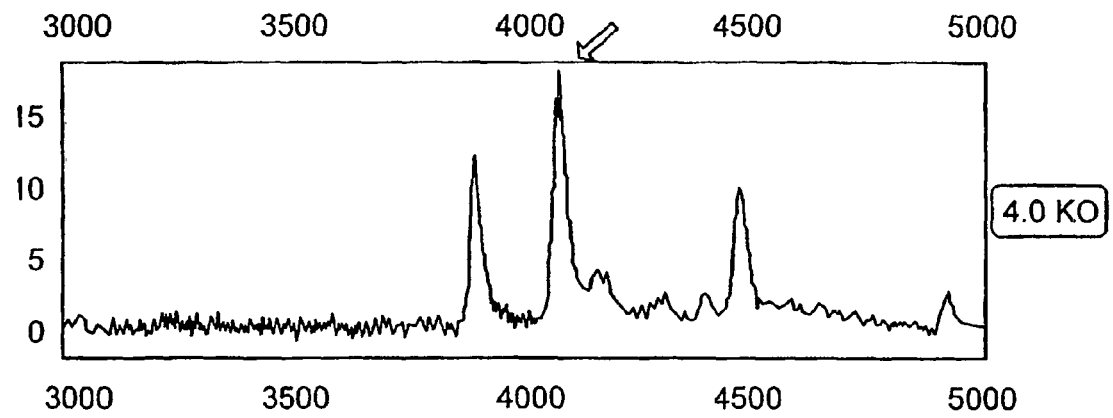
FIG. 1E (Marker V)
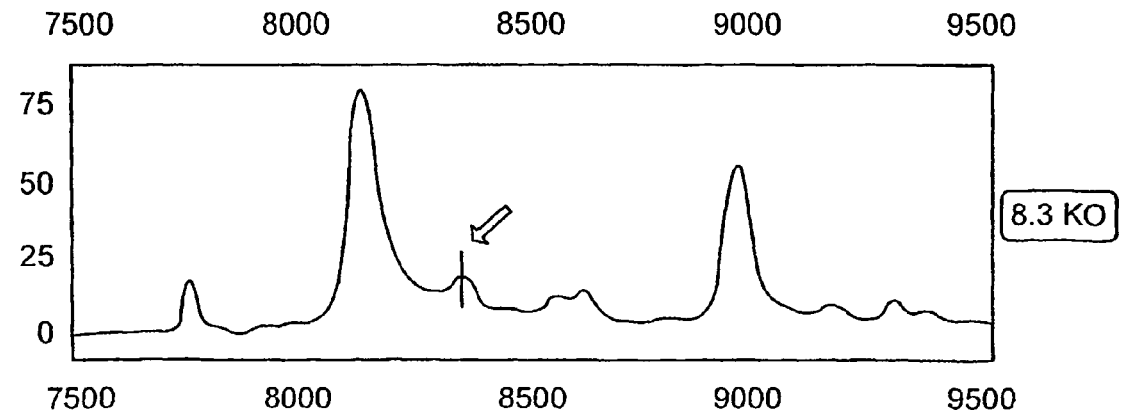
FIG. 1F (Marker VI)

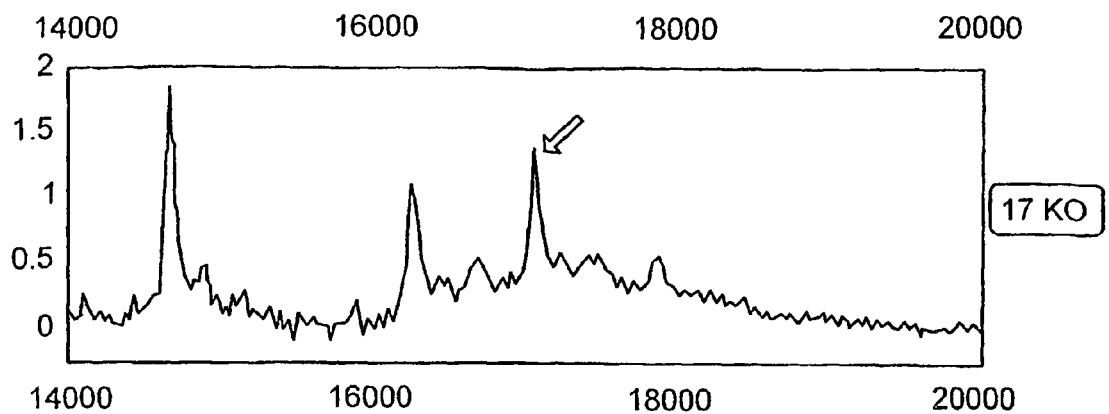
FIG. 1G (Marker VII)
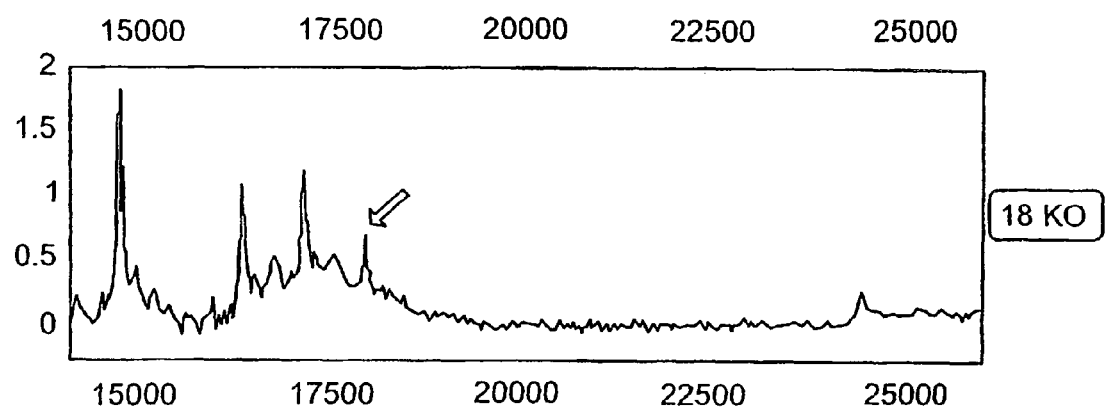
FIG. 1H (Marker VIII)
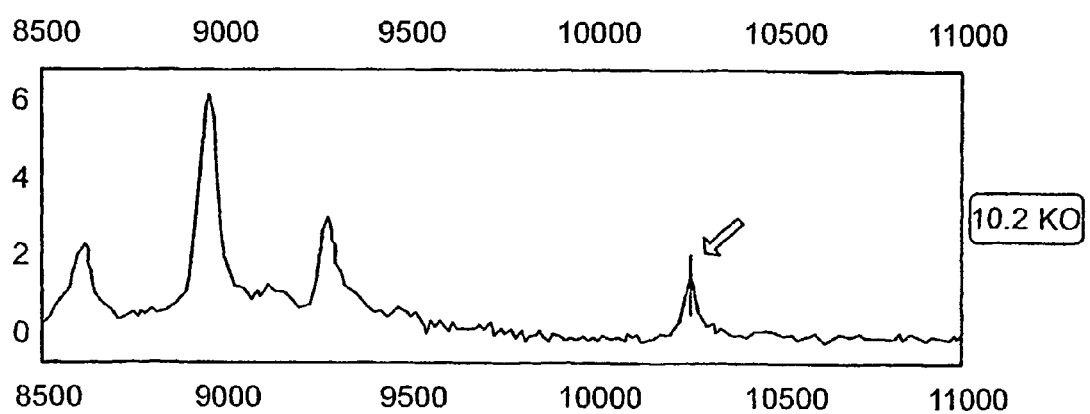
FIG. 1I (Marker IX)

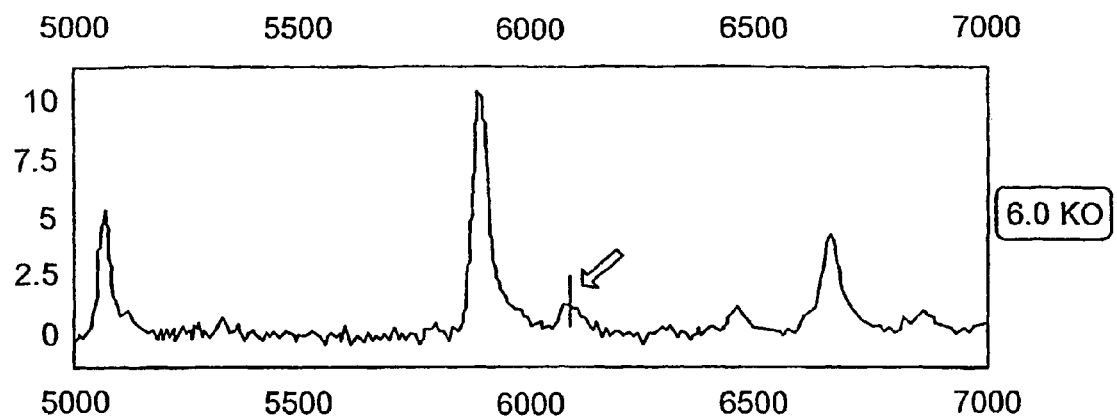
FIG. 1J (Marker X)
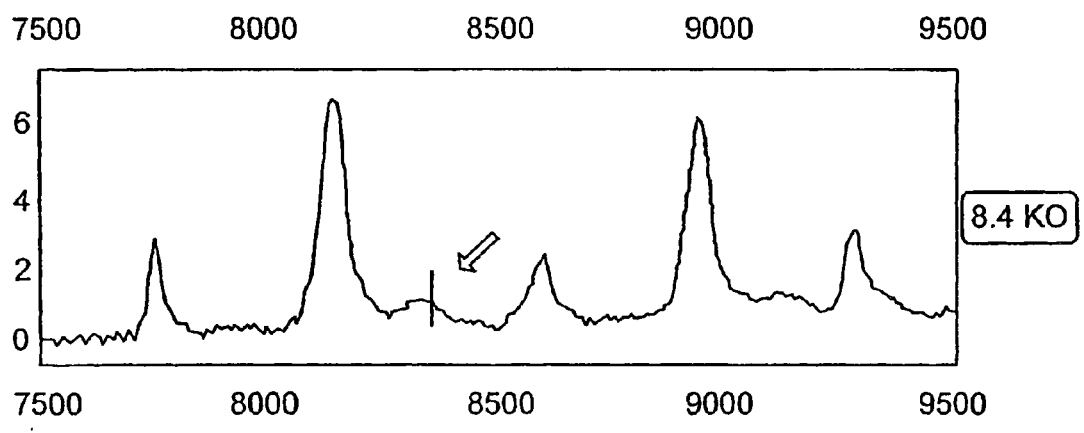
FIG. 1K (Marker XI)
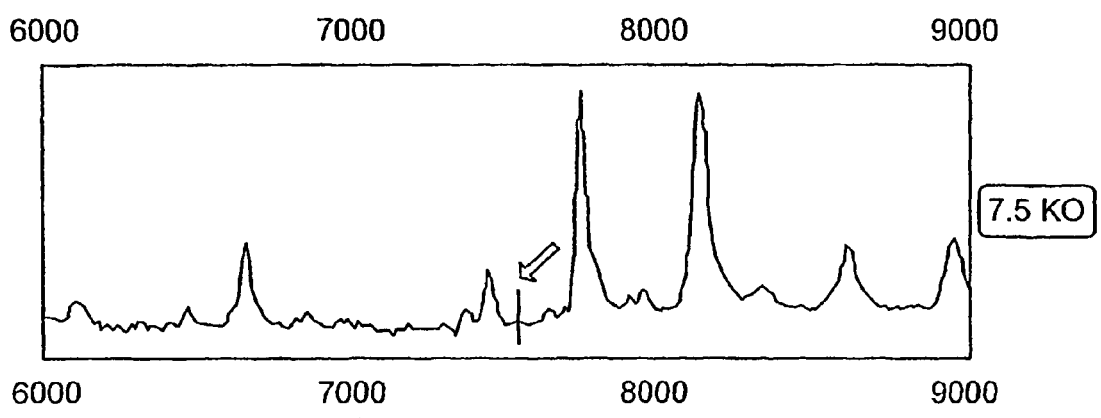
FIG. 1L (Marker XII)

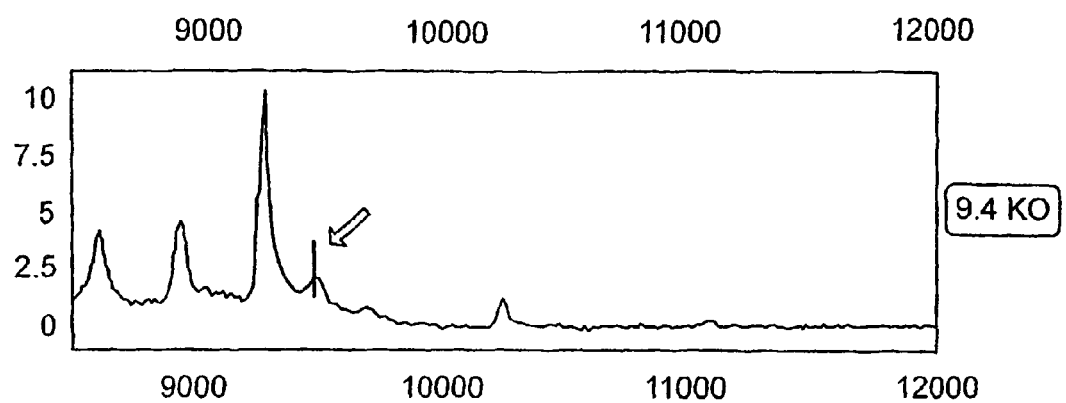
FIG. 1M (Marker XIII)
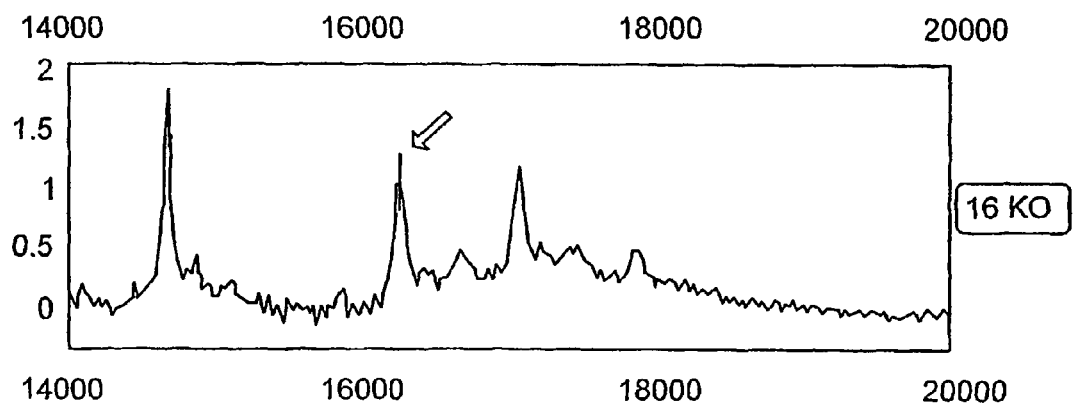
FIG. 1N (Marker XIV)

Sequence for the 8.9 kDa Marker

SVQLTEKRMDKVGKYPKELRKCCEDGM
RENPMRFSCQRRTRFISLGEACKKVFLD
CCNYITELRRQHARASHLGLA

Theoretical pI: 9.54 / Mw (average mass): 8938.46

SEQUENCE LISTING

<160> NUMBER OF SEQ ID NOS: 2

<210> SEQ ID NO 1
<211> LENGTH: 76
<212> TYPE: PRT

-continued

```
<213> ORGANISM: Homo sapiens

<400> SEQUENCE: 1

Ser Val Gln Leu Thr Glu Lys Arg Met Asp Lys Val Gly Lys Tyr Pro
1               5                   10                  15

Lys Glu Leu Arg Lys Cys Cys Glu Asp Gly Met Arg Glu Asn Pro Met
                20                  25                  30

Arg Phe Ser Cys Gln Arg Arg Thr Arg Phe Ile Ser Leu Gly Glu Ala
            35                  40                  45

Cys Lys Lys Val Phe Leu Asp Cys Cys Asn Tyr Ile Thr Glu Leu Arg
            50                  55                  60

Arg Gln His Ala Arg Ala Ser His Leu Gly Leu Ala
65                  70                  75

<210> SEQ ID NO 2
<211> LENGTH: 68
<212> TYPE: PRT
<213> ORGANISM: Homo sapiens

<400> SEQUENCE: 2

Ser Val Gln Leu Thr Glu Lys Arg Met Asp Lys Val Gly Lys Tyr Pro
1               5                   10                  15

Lys Glu Leu Arg Lys Cys Cys Glu Asp Gly Met Arg Glu Asn Pro Met
                20                  25                  30

Arg Phe Ser Cys Gln Arg Arg Thr Arg Phe Ile Ser Leu Gly Glu Ala
            35                  40                  45

Cys Lys Lys Val Phe Leu Asp Cys Cys Asn Tyr Ile Thr Glu Leu Arg
            50                  55                  60

Arg Gln His Ala
65
```

BIOMARKERS FOR BREAST CANCER

The present application claims priority of U.S. provisional application No. 60/610,769, filed Sep. 17, 2004, which is incorporated herein by reference in its entirety.

BACKGROUND OF THE INVENTION

Based on the National Cancer Institute (NCI) incidence and National Center for Health Statistics (NCHS) mortality data, the American Cancer Society estimated that breast cancer would be the most commonly diagnosed cancer among women in 2002 in the United States. It is expected to account for 31 percent (203,500) of all new cancer cases among women and 39,600 will die from this disease. Jemal A, Thomas A, Murray T, Thun M. Cancer statistics, 2002. CA Cancer J. Clin. 2002; 52:23-47. Presymptomatic screening to detect early-stage cancer while it is still respectable with potential for cure can greatly reduce breast cancer related mortality. Unfortunately, only about 50% of the breast cancers are localized at the time of diagnosis. Despite the availability and recommended use of mammography for women age 40 and older as a routine screening method, its effectiveness on reducing overall population mortality from breast cancer is still being investigated. K. Antman et al., JAMA. 1999; 281:1470-2. Currently, serum tumor markers that have been d for use in breast cancer detection still lack the adequate sensitivity and specificity to be applicable in detecting early-stage carcinoma in a large population. The FDA approved tumor markers such as CA15.3 and CA27.29, are only recommended for monitoring therapy of advanced breast cancer or recurrence. D. W. Chan et al., J. Clin. Oncology. 1997; 15:2322-2328. New biomarkers that could be used individually or in combination with an existing modality for cost-effective screening of breast cancer are still urgently needed.

BRIEF SUMMARY OF THE INVENTION

In one aspect, the present invention provides methods for qualifying breast cancer status in a subject comprising measuring at least one biomarker in a biological sample from the subject, wherein the at least one biomarker is selected from the group consisting of the biomarkers of ITIH4 fragment 1 (BC-1), ITIH4 fragment 1b (BC-1b), C3a-desArgΔ8, and C3a-desArg, and correlating the measurement with breast cancer status. In one embodiment, the methods comprise measuring each of: ITIH4 fragment 1 (BC-1), ITIH4 fragment 1b (BC-1b), C3a-desArgΔ8, and C3a-desArg. In another embodiment, the methods further comprise measuring CA15-3.

In one embodiment, the at least one biomarker is measured by capturing the biomarker on an adsorbent surface of a SELDI probe and detecting the captured biomarkers by laser desorption-ionization mass spectrometry. In another embodiment, the at least one biomarker is measured by immunoassay, e.g., using an antibody specific for the at least one biomarker. In a preferred embodiment, the at least one biomarker is detected using a method other than mass spectrometry. In another preferred embodiment, the sample is serum. In still another embodiment, the correlating is performed by a software classification algorithm.

In one embodiment, breast cancer status is selected from breast cancer and non-breast cancer. In another embodiment, breast cancer status is selected from non-invasive breast cancer and invasive breast cancer.

In a further embodiment, the methods comprise managing subject treatment based on the status.

In a preferred embodiment, the adsorbent is a IMAC-Ni adsorbent. In another preferred embodiment, the adsorbent is a biospecific adsorbent (e.g., an antibody).

In another embodiment, if the measurement correlates with breast cancer, then the methods may further comprise managing subject treatment comprises administering a chemotherapeutic agent or radiation to the subject. In still another embodiment, the methods comprise further measuring the at least one biomarker after subject management and correlating the measurement with disease progression.

In another embodiment, methods of the invention comprise measuring at least one biomarker in a sample from a subject, wherein the at least one biomarker is selected from the group consisting of biomarkers of: ITIH4 fragment 1 (BC-1), ITIH4 fragment 1b (BC-1b), C3a-desArgΔ8, and C3a-desArg. In one embodiment, the methods comprise measuring each of the following biomarkers: ITIH4 fragment 1 (BC-1), ITIH4 fragment 1b (BC-1b), C3a-desArgΔ8, and C3a-desArg. In another embodiment, the methods further comprise comprising measuring CA15-3.

In one embodiment, the biomarker is measured by capturing the biomarker on an adsorbent surface of a SELDI probe and detecting the captured biomarkers by laser desorption-ionization mass spectrometry. In a preferred embodiment, the sample is serum. In another embodiment, the adsorbent is an IMAC-Ni adsorbent. In a preferred embodiment, the adsorbent is a biospecific adsorbent (e.g., an antibody).

In another embodiment, the invention provides a kit comprising a solid support comprising at least one capture reagent attached thereto, wherein the capture reagent binds at least one biomarker from a first group consisting of ITIH4 fragment 1 (BC-1), ITIH4 fragment 1b (BC-1b), C3a-desArgΔ8, and C3a-desArg; and instructions for using the solid support to detect the at least one biomarker. In one embodiment, the kit comprises instructions for using the solid support to detect each of the biomarkers: ITIH4 fragment 1 (BC-1), ITIH4 fragment 1b (BC-1b), C3a-desArgΔ8, and C3a-desArg. In another embodiment, the kit provides instructions for using the solid support to detect CA15-3.

In one embodiment, the kit provides a solid support comprising a capture reagent is a SELDI probe. In another embodiment, the capture reagent is an antibody.

In another embodiment, the kit further comprises a container containing at least one of the biomarkers of ITIH4 fragment 1 (BC-1 j), ITIH4 fragment 1b (BC-1b), C3a-desArgΔ8, and C3a-desArg. In another embodiment, the kit further comprises an IMAC-Ni chromatography sorbent.

In another embodiment, the invention provides a kit comprise a solid support comprising at least one capture reagent attached thereto, wherein the capture reagents bind at least one biomarker selected from the group consisting of the biomarkers of ITIH4 fragment 1 (BC-1), ITIH4 fragment 1b (BC-1b), C3a-desArgΔ8, and C3a-desArg; and a container containing at least one of the biomarkers. In one embodiment, the container contains each of the following biomarkers: ITIH4 fragment 1 (BC-1), ITIH4 fragment 1b (BC-1b), C3a-desArgΔ8; and C3a-desArg. In a further embodiment, the container contains CA15-3.

In one embodiment, the solid support comprising a capture reagent is a SELDI probe. In a further embodiment, the kit comprises an IMAC-Ni chromatography sorbent.

In another embodiment, the invention provides a software product comprising: code that accesses data attributed to a sample, the data comprising measurement of at least one biomarker in the sample, the biomarker selected from the group consisting of the biomarkers of ITIH4 fragment 1 (BC-1), ITIH4 fragment 1b (BC-1b), C3a-desArgΔ8, and C3a- desArg; and code that executes a classification algorithm that classifies the breast cancer status of the sample as a function of the measurement. In another embodiment, the classification algorithm classifies the breast cancer status of the sample as a function of the measurement of a biomarker selected from the group consisting of: ITIH4 fragment 1 (BC-1), ITIH4 fragment 1b (BC-1b), C3a-desArgΔ8, and C3a-desArg. In another embodiment, the classification algorithm classifies the breast cancer status of the sample as a function of the measurement of each of the biomarkers: ITIH4 fragment 1 (BC-1), ITIH4 fragment 1b (BC-1b), C3a-desArgΔ8, and C3a-desArg. In another embodiment, the classification algorithm classifies the breast cancer status of the sample further as a function of the measurement of CA15-3.

In another embodiment, the invention provides purified biomolecules selected from the biomarkers ITIH4 fragment 1 (BC-1), ITIH4 fragment 1b (BC-1b), C3a-desArgΔ8, and C3a-desArg.

In another embodiment, the invention provides a method comprising detecting a biomarker selected from the group consisting of ITIH4 fragment 1 (BC-1), ITIH4 fragment 1b (BC-1b), C3a-desArgΔ8, and C3a-desArg by mass spectrometry or immunoassay.

In another embodiment, the invention provides a method comprising communicating to a subject a diagnosis relating to breast cancer status determined from the correlation of biomarkers in a sample from the subject, wherein said biomarkers are selected from the group consisting of ITIH4 fragment 1 (BC-1), ITIH4 fragment 1b (BC-1b), C3a-desArgΔ8, and C3a-desArg 2. In one embodiment, the diagnosis is communicated to the subject via a computer-generated medium.

In another embodiment, the invention provides a method for identifying a compound that interacts with a biomarker selected from the group consisting of ITIH4 fragment 1 (BC-1), ITIH4 fragment 1b (BC-1b), C3a-desArgΔ8, and C3a-desArg wherein said method comprises: contacting the biomarker with a test compound; and determining whether the test compound interacts with the biomarker.

In another embodiment, the invention provides a method for modulating the concentration of a biomarker selected from the group consisting of ITIH4 fragment 1 (BC-1), ITIH4 fragment 1b (BC-1b), C3a-desArgΔ8, and C3a-desArg in a cell, wherein said method comprises: contacting said cell with a test compound, wherein said test compound prevents cleavage of ITIH4 fragment 1 (BC-1), ITIH4 fragment 1b (BC-1b), or C3a-desArgΔ8.

In another embodiment, the invention provides a method of treating a condition in a subject, wherein said method comprises: administering to a subject a therapeutically effective amount of a compound, wherein said compound prevents cleavage of ITIH4 fragment 1 (BC-1), ITIH4 fragment 1b (BC-1b), or C3a-desArgΔ8. In a preferred embodiment, the condition is breast cancer.

BRIEF DESCRIPTION OF THE DRAWINGS

FIGS. 1A through 1N show mass spectra of Markers I through XIV respectively. In those Figures, the mass spectral peak of the specified marker is designated within the depicted spectra with an arrow. The Figure designation is set above each of the referred to spectra.

FIG. 4A shows illustrative results of separation achieved using UMSA derived liner combination of all 147 peaks.

FIG. 4B shows illustrative results of separation achieved using UMSA derived liner combination using the three selected peaks.

FIG. 6A shows the results of 15 peaks selected from Pro-Peak Bootstrap Analysis with rank standard deviation <7.0.

FIG. 6B is a graph showing re-evaluated scores of the selected top 4 peaks from FIG. 6A.

FIG. 8A is a scatter plot showing the results obtained with BC3 alone.

FIG. 8B is a scatter plot showing the results of a logistic regression derived composite index using BC1, BC2 and BC3.

FIG. 12 shows the capture of markers BC-2 (C3a-desArgΔ8) and BC-3 (C3a-desArg) by an antibody against C3a.

FIG. 13 shows the capture of marker BC-2 (C3a-desArgΔ8) by an antibody against C3a.

FIG. 14 shows the capture of marker BC-3 (C3a-desArg) by an antibody against C3a.

FIG. 19 shows the amino acid sequence (SEQ ID NO: 1) of marker BC-3 (C3a-desArg).

DETAILED DESCRIPTION OF THE INVENTION

1. Introduction

Figure 2:
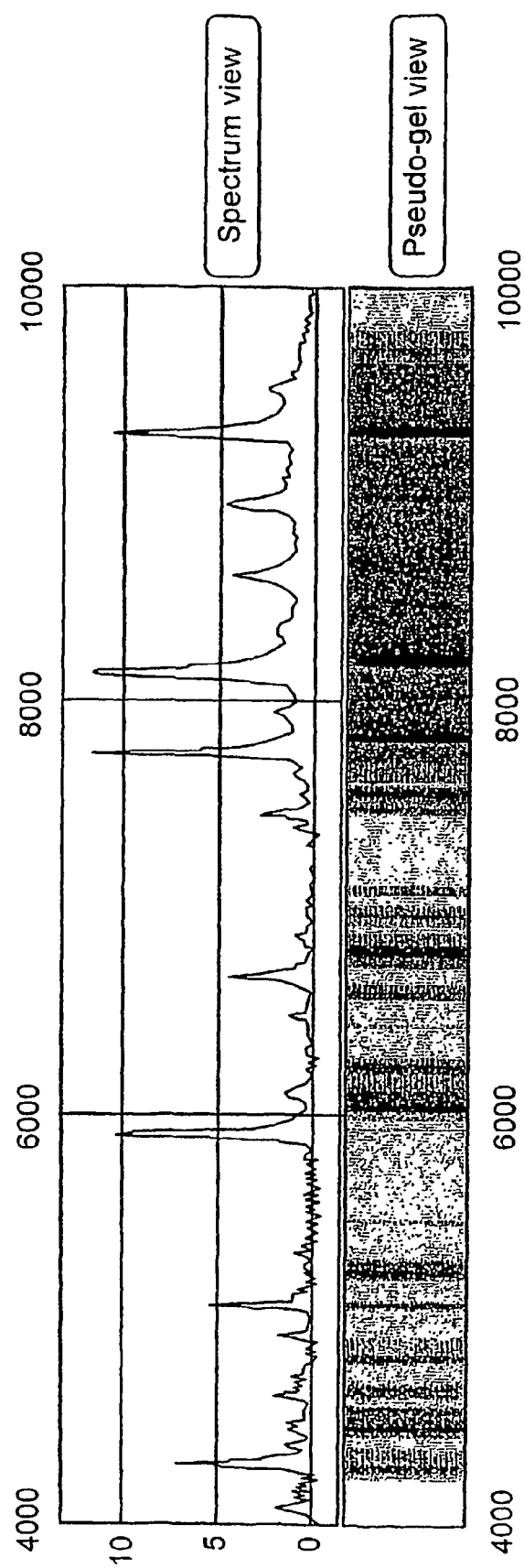
FIG. 2 shows a representative mass peak spectrum obtained by SELDI analysis of serum proteins retained on an IMAC-Ni$^{2+}$ chip. The upper panel shows the spectrum view; the lower panel shows the pseudo-gel view of the same spectrum of M/Z (mass-dependent velocities) between 4,000 and 10,000.

A biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

2. Biomarkers for Breast Cancer 2.1. Biomarkers

This invention provides polypeptide-based biomarkers that are differentially present in subjects having breast cancer, in particular, early-stage breast cancer versus normal (non-breast cancer). The biomarkers are characterized by mass-to-charge ratio as determined by mass spectrometry, by the shape of their spectral peak in time-of-flight mass spectrometry and by their binding characteristics to adsorbent surfaces. These characteristics provide one method to determine whether a particular detected biomolecule is a biomarker of this invention. These characteristics represent inherent characteristics of the biomolecules and not process limitations in the manner in which the biomolecules are discriminated. In one aspect, this invention provides these biomarkers in isolated form.

The biomarkers were discovered using SELDI technology employing ProteinChip arrays from Ciphergen Biosystems, Inc. (Fremont, Calif.) ("Ciphergen"). Serum samples were collected from subjects diagnosed with breast cancer, including ductal carcinoma in situ (DCIS) and invasive breast cancer, and subjects diagnosed as normal, as well as from subjects with benign breast disease. The samples were fractionated by IMAC-Ni (Immobilized Metal Affinity Capture) chromatography. Fractionated samples were applied to SELDI biochips and spectra of polypeptides in the samples were generated by time-of-flight mass spectrometry on a Ciphergen PBSII mass spectrometer. The spectra thus obtained were analyzed by Ciphergen Express™ Data Manager Software with Biomarker Wizard and Biomarker Pattern Software from Ciphergen Biosystems, Inc. The mass spectra for each group were subjected to scatter plot analysis. A Mann-Whitney test analysis was employed to compare breast cancer and control groups for each protein cluster in the scatter plot, and proteins were selected that differed significantly ($p<0.0001$) between the two groups. This method is described in more detail in the Example Section.

In parallel with the SELDI evaluation, we have determined the protein identity of three of the markers.

BC-1, with m/z of about 4.3 KD, was identified as a fragment ("fragment 1") of human inter-alpha trypsin inhibitor, heavy chain H4 (also referred to as "ITIH4", "IAIH4, or "PK-120"). An alternate form of BC-1, designated "BC-1b" or "ITIH4 fragment 1b", was also identified. ITIH4 fragment 1b has an m/z of about 4.6 KD. Both ITIH4 fragments 1 and 2 contain an epitope recognized by antibody to ITIH4 which is present in a biomarker that is correlated with ovarian cancer.

BC-2, with m/z of 8.1 KD, is a truncated form of C3a-desArg (referred to as C3a-desArg-8.1 or C3a-desArgΔ8). The amino acid sequence of C3a-desArgΔ8 is SVQLTEKRMDKVGKYPKELRKCCEDGM-RENPMRFSCQRRTRFISLGEACKKVFLDC CNYITEL-RRQHA (SEQ ID NO:2). This form has a theoretical mass of 8132 daltons, and the predicted pI is 9.38.

BC-3, m/z of 8.9 KD, is identified as C3a-desArg. The amino acid sequence of C3a-desArg is SVQLTEKRMD-KVGKYPKELRKCCEDGMRENPMRFSCQR-RTRFISLGEACKKVFLDC CNYITELRRQHA-RASHLGLA, set forth as SEQ ID NO: 1. Its predicted mass is 8923 daltons, consistent with the measured mass of 8926 daltons, and the predicted pI is 9.54, consistent with its inability to bind anion exchange resin at pH 9.0.

The biomarkers thus discovered are presented in Table 1. The "ProteinChip assay" column refers to chromatographic fraction in which the biomarker is found, the type of biochip to which the biomarker binds and the wash conditions, as per the Example.

TABLE 1

| Marker | P-Value | Up or down regulated in breast cancer | ProteinChip ® assay |
|---|---|---|---|
| ITIH4 frag. 1 (BC-1); M4283 | <0.0001 | Down | IMAC—Ni, wash with PBS |
| ITIH4 frag. 1b (BC-1b); M4635 | <0.0001 | Down | IMAC—Ni, wash with PBS |
| C3a-desArgΔ8 (BC-2); M8116 | <0.0001 | Up | IMAC—Ni, wash with PBS |
| C3a-desArg (BC-3); M8926 | <0.0001 | Up | IMAC—Ni, wash with PBS |

The biomarkers of this invention are characterized by their mass-to-charge ratio as determined by mass spectrometry. The mass-to-charge ratio of each biomarker is provided in Table 1 after the "M." Thus, for example, M4283 has a measured mass-to-charge ratio of 4283. The mass-to-charge ratios were determined from mass spectra generated on a Ciphergen Biosystems, Inc. PBS II mass spectrometer. This instrument has a mass accuracy of about +/0.15 percent. Additionally, the instrument has a mass resolution of about 400 to 1000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII, taking the maximum and minimum mass-to-charge-ratio in the cluster, and dividing by two. Accordingly, the masses provided reflect these specifications.

The biomarkers of this invention are further characterized by the shape of their spectral peak in time-of-flight mass spectrometry. Mass spectra showing peaks representing the biomarkers are presented in FIG. 1.

The biomarkers of this invention are further characterized by their binding properties on chromatographic surfaces. Most of the biomarkers bind to metal chelate adsorbents (e.g., the Ciphergen® IMAC-Ni ProteinChip® array) after washing with PBS.

Further characterization of the biomarkers can be found in International Publication no WO 03/076896, the entire contents of which are incorporated herein by reference.

The identity of certain of the biomarkers of this invention has been determined and is indicated in Table 1. The method by which this determination was made is described in the Example Section. For biomarkers whose identify has been determined, the presence of the biomarker can be determined by other methods known in the alt.

Because the biomarkers of this invention are characterized by mass-to-charge ratio, binding properties and spectral shape, they can be detected by mass spectrometry without knowing their specific identity. However, if desired, biomarkers whose identity is not determined can be identified by, for example, determining the amino acid sequence of the polypeptides. For example, a biomarker can be peptide-mapped with a number of enzymes, such as trypsin or V8 protease, and the molecular weights of the digestion fragments can be used to search databases for sequences that match the molecular weights of the digestion fragments generated by the various enzymes. Alternatively, protein biomarkers can be sequenced using tandem MS technology. In this method, the protein is isolated by, for example, gel electrophoresis. A band containing the biomarker is cut out and the protein is subject to protease digestion. Individual protein fragments are separated by a first mass spectrometer. The fragment is then subjected to collision-induced cooling, which fragments the peptide and produces a polypeptide ladder. A polypeptide ladder is then analyzed by the second mass spectrometer of the tandem MS. The difference in masses of the members of the polypeptide ladder identifies the amino acids in the sequence. An entire protein can be sequenced this way, or a sequence fragment can be subjected to database mining to find identity candidates.

The preferred biological source for detection of the biomarkers is urine. However, in other embodiments, the biomarkers can be detected in serum.

The biomarkers of this invention are biomolecules. Accordingly, this invention provides these biomolecules in isolated form. The biomarkers can be isolated from biological fluids, such as urine or serum. They can be isolated by any method known in the art, based on both their mass and their binding characteristics. For example, a sample comprising the biomolecules can be subject to chromatographic fractionation, as described herein, and subject to further separation by, e.g., acrylamide gel electrophoresis. Knowledge of the identity of the biomarker also allows their isolation by immunoaffinity chromatography.

2.2. Use of Modified Forms of a Biomarker

It has been found that proteins frequently exist in a sample in a plurality of different forms characterized by a detectably different mass. These forms can result from either, or both, of pre- and post-translational modification. Pre-translational modified forms include allelic variants, slice variants and RNA editing forms. Post-translationally modified forms include forms resulting from proteolytic cleavage (e.g., fragments of a parent protein), glycosylation, phosphorylation, lipidation, oxidation, methylation, cystinylation, sulphonation and acetylation. The collection of proteins including a specific protein and all modified forms of it is referred to herein as a "protein cluster." The collection of all modified forms of a specific protein, excluding the specific protein, itself, is referred to herein as a "modified protein cluster." Modified forms of any biomarker of this invention (including any of Markers ITIH4 fragment 1, ITIH4 fragment 1b, C3a-desArgΔ8, and/or C3a-desArg) also may be used, themselves, as biomarkers. In certain cases the modified forms may exhibit better discriminatory power in diagnosis than the specific forms set forth herein.

Modified forms of a biomarker including any of Markers ITIH4 fragment 1, ITIH4 fragment 1b, C3a-desArgΔ8, and/or C3a-desArg can be initially detected by any methodology that can detect and distinguish the modified from the biomarker. A preferred method for initial detection involves first capturing the biomarker and modified forms of it, e.g., with biospecific capture reagents, and then detecting the captured proteins by mass spectrometry. More specifically, the proteins are captured using biospecific capture reagents, such as antibodies, aptamers or Affibodies that recognize the biomarker and modified forms of it. This method also will also result in the capture of protein interactors that are bound to the proteins or that are otherwise recognized by antibodies and that, themselves, can be biomarkers. Preferably, the biospecific capture reagents are bound to a solid phase. Then, the captured proteins can be detected by SELDI mass spectrometry or by eluting the proteins from the capture reagent and detecting the eluted proteins by traditional MALDI or by SELDI. The use of mass spectrometry is especially attractive because it can distinguish and quantify modified forms of a protein based on mass and without the need for labeling.

Preferably, the biospecific capture reagent is bound to a solid phase, such as a bead, a plate, a membrane or a chip. Methods of coupling biomolecules, such as antibodies, to a solid phase are well known in the art. They can employ, for example, bifunctional linking agents, or the solid phase can be derivatized with a reactive group, such as an epoxide or an imidizole, that will bind the molecule on contact. Biospecific capture reagents against different target proteins can be mixed in the same place, or they can be attached to solid phases in different physical or addressable locations. For example, one can load multiple columns with derivatized beads, each column able to capture a single protein cluster. Alternatively, one can pack a single column with different beads derivatized with capture reagents against a variety of protein clusters, thereby capturing all the analytes in a single place. Accordingly, antibody-derivatized bead-based technologies, such as xMAP technology of Luminex (Austin, Tex.) can be used to detect the protein clusters. However, the biospecific capture reagents must be specifically directed toward the members of a cluster in order to differentiate them.

In yet another embodiment, the surfaces of biochips can be derivatized with the capture reagents directed against protein clusters either in the same location or in physically different addressable locations. One advantage of capturing different clusters in different addressable locations is that the analysis becomes simpler.

After identification of modified forms of a protein and correlation with the clinical parameter of interest, the modified form can be used as a biomarker in any of the methods of this invention. At this point, detection of the modified from can be accomplished by any specific detection methodology including affinity capture followed by mass spectrometry, or traditional immunoassay directed specifically the modified form. Immunoassay requires biospecific capture reagents, such as antibodies, to capture the analytes. Furthermore, if the assay must be designed to specifically distinguish protein and modified forms of protein. This can be done, for example, by employing a sandwich assay in which one antibody captures more than one form and second, distinctly labeled antibodies, specifically bind, and provide distinct detection of, the various forms. Antibodies can be produced by immunizing animals with the biomolecules. This invention contemplates traditional immunoassays including, for example, sandwich immunoassays including ELISA or fluorescence-based immunoassays, as well as other enzyme immunoassays.

3. Detection of Biomarkers for Breast Cancer

The biomarkers of this invention can be detected by any suitable method. Detection paradigms that can be employed to this end include optical methods, electrochemical methods (voltammetry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of polypeptides. Many protein biochips are described: in the art. These include; for example, protein biochips produced by Ciphergen Biosystems, Inc. (Fremont, Calif.), Packard BioScience Company (Meriden Conn.), Zyomyx (Hayward, Calif.), Phylos (Lexington, Mass.) and Biacore (Uppsala, Sweden). Examples of such protein biochips are described in the following patents or published patent applications: U.S. Pat. No. 6,225,047; PCT International Publication No. WO 99/51773; U.S. Pat. No. 6,329,209, PCT International Publication No. WO 00/56934 and U.S. Pat. No. 5,242,828.

3.1. Detection by Mass Spectrometry

In a preferred embodiment, the biomarkers of this invention are detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer.

3.1.1. SELDI

A preferred mass spectrometric technique for use in the invention is "Surface Enhanced Laser Description and Ionization" or "SELDI," as described, for example, in U.S. Pat. No. 5,719,060 and No. 6,225,047, both to Hutchens and Yip. This refers to a method of desorption/ionization gas phase ion spectrometry (e.g., mass spectrometry) in which an analyte (here, one or more of the biomarkers) is captured on the surface of a SELDI mass spectrometry probe. There are several versions of SELDI.

One version of SELDI is called "affinity capture mass spectrometry." It also is called "Surface-Enhanced Affinity Capture" or "SEAC". This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent may be attached directly to the substrate of the selective surface, or the substrate may have a reactive surface that carries a reactive moiety that is capable of binding the capture reagent, e.g., through a reaction forming a covalent or coordinate covalent bond. Epoxide and carbodiimidizole are useful reactive moieties to covalently bind polypeptide capture reagents such as antibodies or cellular receptors. Nitriloacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen ProteinChip® arrays include NP20 (hydrophilic); H4 and H50 (hydrophobic); SAX-2, Q-10 and LSAX-30 (anion exchange); WCX-2, CM-10 and LWCX-30 (cation exchange); IMAC-3, IMAC-30 and IMAC 40 (metal chelate); and PS-10, PS-20 (reactive surface with carboimidizole, expoxide) and PG-20 (protein G coupled through carboimidizole). Hydrophobic ProteinChip arrays have isopropyl or nonylphenoxypoly(ethylene glycol)methacrylaate functionalities. Anion exchange ProteinChip arrays have quaternary ammonium functionalities. Cation exchange ProteinChip arrays have carboxylate functionalities. Immobilized metal chelate ProteinChip arrays have have nitriloacetic acid functionalities that adsorb transition metal ions, such as copper, nickel, zinc, and gallium, by chelation. Preactivated ProteinChip arrays have carboimidizole or epoxide functional groups that can react with groups on proteins for covalent binding.

Such biochips are further described in: U.S. Pat. No. 6,579, 719 (Hutchens and Yip, "Retentate Chromatography," Jun. 17, 2003); PCT International Publication No. WO 00/66265 (Rich et al., "Probes for a Gas Phase Ion Spectrometer," Nov. 9, 2000); U.S. Pat. No. 6,555,813 (Beecher et al., "Sample Holder with Hydrophobic Coating for Gas Phase Mass Spectrometer," Apr. 29, 2003); U.S. Patent Application No. U.S. 2003 0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Patent Application No. US 2003/ 0218130 A1 (Boschetti et al., "Biochips With Surfaces Coated With Polysaccharide-Based Hydrogels," Apr. 14, 2003) and U.S. Patent Application No. 60/448,467, entitled "Photocrosslinked Hydrogel Surface Coatings" (Huang et al., filed Feb. 21, 2003).

In general, a probe with an adsorbent surface is contacted with the sample for a period of time sufficient to allow biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Another version of SELDI is Surface-Enhanced Neat Desorption (SEND), which involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyacetophenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecylmethacrylate ("C18 SEND"). SEND is further described in U.S. Pat. No. 6,124,137 and PCT international Publication No. WO 03/64594 (Kitagawa, "Monomers And Polymers Having Energy Absorbing Moieties Of Use In Desorption/Ionization Of Analytes," Aug. 7, 2003).

SEAC/SEND is a version of SELDI in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

Another version of SELDI, called Surface-Enhanced Photolabile Attachment and Release (SEPAR), involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

3.1.2. Other Mass Spectrometry Methods

In another mass spectrometry method, the biomarkers can be first captured on a chromatographic resin having chromatographic properties that bind the biomarkers. In the present example, this could include a variety of methods. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

3.1.3. Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set at zero in the scale.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (N/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

3.1.4. General Protocol for SELDI Detection of Biomarkers for Breast Cancer

A preferred protocol for the detection of the biomarkers of this invention is as follows. The biological sample to be tested, e.g., serum or urine, preferably is subject to pre-fractionation before SELDI analysis. This simplifies the sample and improves sensitivity. A preferred method of pre-fractionation involves contacting the sample with an anion exchange chromatographic material, such as Q HyperD (BioSepra, SA). The bound materials are then subject to stepwise pH elution using buffers at pH 9, pH 7, pH 5 and pH 4. (See Example 1—Buffer list.) (The fractions in which the biomarkers are eluted also is indicated in Table 1.) Various fractions containing the biomarker are collected.

The sample to be tested (preferably pre-fractionated) is then contacted with an affinity capture probe comprising an cation exchange adsorbent (preferably a WCX ProteinChip array (Ciphergen Biosystems, Inc.)) or an IMAC adsorbent (preferably an IMAC3 ProteinChip array (Ciphergen Biosystems, Inc.)), again as indicated in Table 1. The probe is washed with a buffer that will retain the biomarker while washing away unbound molecules. A suitable wash for each biomarker is the buffer identified in Table 1. The biomarkers are detected by laser desorption/ionization mass spectrometry.

Alternatively, if antibodies that recognize the biomarker are available, for example in the case of ITIH4 or C3a-desArg, these can be attached to the surface of a probe, such as a pre-activated PS10 or PS20 ProteinChip array (Ciphergen Biosystems, Inc.). These antibodies can capture the biomarkers from a sample onto the probe surface. Then the biomarkers can be detected by, e.g., laser desorption/ionization mass spectrometry.

3.2. Detection by Immunoassay

In another embodiment, the biomarkers of this invention can be measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, sandwich immunoassays including ELISA or fluorescence-based immunoassays, as well as other enzyme immunoassays. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

4. Determination of Subject Breast Cancer Status 4.1. Single Markers

The biomarkers of the invention can be used in diagnostic tests to assess breast cancer status in a subject, e.g., to diagnose early-stage breast cancer. The phrase "breast cancer status" includes any distinguishable manifestation of the disease, including non-disease. For example, disease status includes, without limitation, the presence or absence of disease (e.g., breast cancer v. non-breast cancer), the risk of developing disease, the stage of the disease (e.g., non-invasive or early-stage breast cancer v. invasive or metastatic breast cancer), the progress of disease (e.g., progress of disease or remission of disease over time) and the effectiveness or response to treatment of disease. Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of actual positives who test as positive. Negative predictive value is the percentage of actual negatives that test as negative.

The biomarkers of this invention show a statistical difference in different breast cancer statuses of at least $p \leq 0.05$, $p \leq 10^{-2}$, $p \leq 10^{-3}$, $p \leq 10^{-4}$ or $p \leq 10^{-5}$. Diagnostic tests that use these biomarkers alone or in combination show a sensitivity and specificity of at least 75%, at least 80%, at least 85%, at least 90%, at least 95%, at east 98% and about 100%.

Each biomarker listed in Table 1 is differentially present in breast cancer, and, therefore, each is individually useful in aiding in the determination of breast cancer status. The method involves, first, measuring the selected biomarker in a subject, sample using the methods described herein, e.g. capture on a SELDI biochip followed by detection by mass spectrometry and, second, comparing the measurement with a diagnostic amount or cut-off that distinguishes a positive breast cancer status from a negative breast cancer status. The diagnostic amount represents a measured amount of a biomarker above which or below which a subject is classified as having a particular breast cancer status. For example, if the biomarker is up-regulated compared to normal during breast cancer, then a measured amount above the diagnostic cutoff provides a diagnosis of breast cancer. Alternatively, if the biomarker is down-regulated during breast cancer, then a measured amount below the diagnostic cutoff provides a diagnosis of breast cancer. As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different breast cancer statuses, as was done here, and drawing the cut-off to suit the diagnostician's desired levels of specificity and sensitivity.

4.2. Combinations of Markers

While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test.

4.3. Determining Risk of Developing Disease

In one embodiment, this invention provides methods for determining the risk of developing disease in a subject. Biomarker amounts or patterns are characteristic of various risk states, e.g., high, medium or low. The risk of developing a disease is determined by measuring the relevant biomarker or biomarkers and then either submitting them to a classification algorithm or comparing them with a reference amount and/or pattern of biomarkers that is associated with the particular risk level.

4.4. Determining Stage of Disease

In one embodiment, this invention provides methods for determining the stage of disease in a subject. Each stage of the disease has a characteristic amount of a biomarker or relative amounts of a set of biomarkers (a pattern). The stage of a disease is determined by measuring the relevant biomarker or biomarkers and then either submitting them to a classification algorithm or comparing them with a reference amount and/or pattern of biomarkers that is associated with the particular stage. For example, detection biomarkers ITIH4 fragment 1, ITIH4 fragment 1b, C3a-desArgΔ8, and/or 3a-desArg can be used to distinguish between early-stage (non-invasive) to invasive breast cancer.

4.5. Determining Course (Progression/Remission) of Disease

In one embodiment, this invention provides methods for determining the course of disease in a subject. Disease course refers to changes in disease status over time, including disease progression (worsening) and disease regression (improvement). Over time, the amounts or relative amounts (e.g., the pattern) of the biomarkers changes. For example, biomarkers ITIH4 fragment 1, ITIH4 fragment 1b, C3a-desArgΔ8, and/or C3a-desArg are decreased in disease. Therefore, the trend of these markers, either increased or decreased over time toward diseased or non-diseased indicates the course of the disease. Accordingly, this method involves measuring one or more biomarkers in a subject at least two different time points, e.g., a first time and a second time, and comparing the change in amounts, if any. The course of disease is determined based on these comparisons. Similarly, this method is useful for determining the response to treatment. If a treatment is effective, then the biomarkers will trend toward normal, while if treatment is ineffective, the biomarkers will trend toward disease indications.

4.6. Subject Management

In certain embodiments of the methods of qualifying breast cancer status, the methods further comprise managing subject treatment based on the status. Such management includes the actions of the physician or clinician subsequent to determining breast cancer status. For example, if a physician makes a diagnosis of breast cancer, then a certain regime of treatment, such as prescription or administration of chemotherapy or radiation might follow. Alternatively, a diagnosis of non-breast cancer or benign breast-disease might be followed with further testing to determine a specific disease that might the patient might be suffering from. Also, if the diagnostic test gives an inconclusive result on breast cancer status, further tests may be called for.

Additional embodiments of the invention relate to the communication of assay results or diagnoses or both to technicians, physicians or patients, for example. In certain embodiments, computers will be used to communicate assay results or diagnoses or both to interested parties, e.g.: physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the presence or absence in a test subject of any the biomarkers of Table 1 is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

5. Generation of Classification Algorithms for Qualifying Breast Cancer Status In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application No. 2002 0193950 A1 (Gavin et al., "Method or analyzing mass spectra"), U.S. Patent Application No. 2003 0004402 A1 (Hitt et al., "Process for discriminating between biological states based on hidden patterns from biological data"), and U.S. Patent Application No. 2003 0055615 A1 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, Cow, visual basic, etc.

The learning algorithms described above are useful both for developing classification algorithms for the biomarkers already discovered, or for finding new biomarkers for breast cancer. The classification algorithms, in turn, form the base for diagnostic tests by providing diagnostic values (e.g. cut-off points) for biomarkers used singly or in combination.

6. Kits for Detection of Biomarkers for Breast Cancer

In another aspect, the present invention provides kits for qualifying breast cancer status, which kits are used to detect biomarkers according to the invention. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecific capture reagents, the kit can comprise a solid support with a reactive surface, and a container comprising the biospecific capture reagent.

The kit can also comprise a washing solution or instructions for malting a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

7. Use of Biomarkers for Breast Cancer in Screening Assays and Methods of Treating Breast Cancer The methods of the present invention have other applications as well. For example, the biomarkers can be used to screen for compounds that modulate the expression of the biomarkers in vitro or in vivo, which compounds in turn may be useful in treating or preventing breast cancer in patients. In another example, the biomarkers can be used to monitor the response to treatments for breast cancer. In yet another example, the biomarkers can be used in heredity studies to determine if the subject is at risk for developing breast cancer.

Thus, for example, the kits of this invention could include a solid substrate having a hydrophobic function, such as a protein biochip (e.g., a Ciphergen H50 ProteinChip array, e.g., ProteinChip array) and a sodium acetate buffer for washing the substrate, as well as instructions providing a protocol to measure the biomarkers of this invention on the chip and to use these measurements to diagnose breast cancer.

Compounds suitable for therapeutic testing may be screened initially by identifying compounds which interact with one or more biomarkers listed in Table 1. By way of example, screening might include recombinantly expressing a biomarker listed in Table 1, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave one or more biomarkers of Table 1, in which case the proteins may be detected by monitoring the digestion of one or more biomarkers in a standard assay, e.g., by gel electrophoresis of the proteins.

In a related embodiment, the ability of a test compound to inhibit the activity of one or more of the biomarkers of Table I may be measured. One of skill in the art will recognize that the techniques used to measure the activity of a particular biomarker will vary desponding on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of one of the biomarkers of Table I may also be measured. For example, the self-assembly of a multi-protein complex which includes one of the biomarkers of Table I may be monitored by spectroscopy in the presence or absence of a test compound. Alternatively, if the biomarker is a non-enzymatic enhancer of transcription, test compounds which interfere with the ability of the biomarker to enhance transcription may be identified by measuring the levels of biomarker-dependent transcription in vivo or in vitro in the presence and absence of the test compound.

Test compounds capable of modulating the activity of any of the biomarkers of Table I may be administered to patients who are suffering from or are at risk of developing breast cancer or other cancer. For example, the administration of a test compound which increases the activity of a particular biomarker may decrease the risk of breast cancer in a patient if the activity of the particular biomarker in vivo prevents the accumulation of proteins for breast cancer. Conversely, the administration of a test compound which decreases the activity of a particular biomarker may decrease the risk of breast cancer in a patient if the increased activity of the biomarker is responsible, at least in part, for the onset of breast cancer.

In an additional aspect, the invention provides a method for identifying compounds useful for the treatment of disorders such as breast cancer which are associated with increased levels of modified forms of ITIH4 fragment 1, ITIH4 fragment 1b, C3a-desArg$\Delta$8, and/or C3a-desArg. For example, in one embodiment, cell extracts or expression libraries may be screened for compounds which catalyze the cleavage of full-length ITIH4 or C3a-desArg to form truncated forms. In one embodiment of such a screening assay, cleavage of the biomarkers may be detected by attaching a fluorophore to the biomarker, which remains quenched when the biomarkers is uncleaved, but which fluoresces when the protein is cleaved. Alternatively, a version of full-length biomarker modified so as to render the amide bond between certain amino acids uncleavable may be used to selectively bind or "trap" the cellular protease which cleaves full-length biomarker at that site in vivo. Methods for screening and identifying proteases and their targets are well-documented in the scientific literature, e.g., in Lopez-Ottin et al. (Nature Reviews, 3:509-519 (2002

In yet another embodiment, the invention provides a method for treating or reducing the progression or likelihood of a disease, e.g., breast cancer, which is associated with the increased levels of truncated ITIH4 or C3a-desArg. For example, after one or more proteins have been identified which cleave full-length the biomarkers, combinatorial libraries may be screened for compounds which inhibit the cleavage activity of the identified proteins. Methods of screening chemical libraries for such compounds are well-known in art. See, e.g., Lopez-Otin et al. (2002). Alternatively, inhibitory compounds may be intelligently designed based on the structure of ITIH4 or C3a-desArg.

At the clinical level, screening a test compound includes obtaining samples from test subjects before and after the subjects have been exposed to a test compound. The levels in the samples of one or more of the biomarkers listed in Table 1 may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of one or more of the biomarkers listed in Table 1 may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which express, or are capable of expressing, one or more of the biomarkers of Table 1 may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with breast cancer, test compounds will be screened for their ability to slow or stop the progression of the disease.

8. Examples

In the following Examples, the following Materials and Methods were used.

Samples.

Retrospective serum-samples were obtained from the Johns Hopkins Clinical Chemistry serum banks, according to the approved protocol by the Johns Hopkins Joint Committee on Clinical Investigation. A total of 169 specimens were included in this study. The cancer group consisted 103 serum samples from breast cancer patients at different clinical stages: Stage 0 (n=4), Stage I (n=38), Stage II (n=37) and Stage III (n=24). Diagnoses were pathologically confirmed and specimens were obtained prior to treatment. Age information was not available on six of these patients. The median age of the remaining 96 patients was 56 years, ranging from 34 to 87 years. The non-cancer control group included serum from 25 with benign breast diseases (BN) and 41 healthy women (HC). Exact age information was not available from 21 healthy women. The median age of the remaining 20 healthy women was 45 years, ranging from 39 to 57 years. The median age of the benign condition group was 48 years with range between 21 and 78 years. All samples were stored at −80° C. until use.

ProteinChip Analysis.

To 20 µl of each serum sample, 30 µl of 8M urea, 1% CHAPS in PBS, PH 7.4 was added. The mixture was vortexed at 4° C. for 15 minutes and diluted 1:40 in PBS. Immobilized metal affinity capture chips (IMAC3) were activated with 50 mM NiSO$_4$ according to manufacturer's instructions (Ciphergen Biosystems, Inc., CA). 50 µl of diluted samples were applied to each spot on the ProteinChip array by using a 96 well bioprocessor (Ciphergen Biosystems, Inc., CA). After binding at room temperature for 60 minutes on a platform shaker, the array was washed twice with 100 μl of PBS for 5 minutes followed by two quick rinses with 100 μl of $dH_2O$. After air-drying, 0.5 μl of saturated sinapinic acid (SPA) prepared in 50% acetonitrile, 0.5% trifluoroacetic acid was applied twice to each spot. Proteins bound to the chelated metal (through histidine, tryptophan, cysteine or phosphorylated amino acids) were detected on a PBS-II mass reader. Data was collected by averaging 80 laser shots with an intensity of 240 and a detector sensitivity of 8. Reproducibility was estimated using two representative serum samples, one from the healthy controls and one from the cancer patients. Each serum sample was spotted on all 8 bait surfaces of one IMAC-Ni chip in each of the two bioprocessors. Coefficience of variance was estimated for the selected mass peaks.
Bioinformatics and Biostatistics.

Qualified mass peaks (S/N>5, cluster mass window at 0.3%) with M/Z between 2K and 150K were selected and the peak intensities were normalized to the total ion current using ProteinChip Software 3.0 (Ciphergen Biosystems, Inc., CA). Further preprocessing steps included logarithmic transformation applied to the peak intensity data in order to obtain a more consistent level of data variance across the entire range of spectrum of interest (M/Z 2 kD-150 kD).

The software package ProPeak (3Z Informatics, SC) was used to compute and rank the contribution of each individual peak towards the optimal separation of two diagnostic groups. ProPeak implements the linear version of the Unified Maximum Separability Analysis (UMSA) algorithm that was first reported for use in microarray data analysis. Z. Zhang et-al., Applying Classification Separability Analysis to Microarray Data, in Proc. of Critical Assessment of Techniques for Microarray Data Analysis (CAMDA'00), Kluwer Academic Publishers, 2001. The key feature of the UMSA algorithm is the incorporation of data-distribution information into a structural risk minimization-learning algorithm (Vapnik V N, Statistical Learning Theory, John Wiley & Sons, Inc., New York, 199814) to identify a direction along which the two classes of data are best separated. This direction is represented as a linear combination (weighted sum) of the original variables. The weight assigned to each variable in this combination measures the contribution of the variable towards the separation of the two classes of data.

ProPeak offers three UMSA based analytical modules. The first is a Component Analysis module, which projects each specimen as an individual point onto a three-dimensional component space. The components (axes) are liner combinations of the original spectrum peak intensities. The axes correspond to directions along which two pre-specified groups of data achieve maximum separability. The separation between the two groups of data can be inspected in an interactive 3D display. The second module is Stepwise Selection, which uses a backward stepwise selection process to apply UMSA to compute a significance score for individual peaks and rank them according to their collective contribution towards the maximal separation of the two pre-specified groups of data. A positive or negative score indicates a relatively elevated or decreased expression level of the corresponding mass peak for the diseased group whereas the absolute value of the score represents its relative importance towards data separation. To avoid selecting peaks-based on only unrelated artifacts in the data, the third module of ProPeak, BootStrap, uses a boot strap procedure to repeat UMSA for multiple runs each time randomly leaving out a fixed percentage of the samples from both groups. The median and mean ranks and the corresponding standard deviation are estimated for each peak. A potential biomarker should be a peak of top median and mean ranks and a minimum rank standard deviation. As a way to establish an objective selection criterion, the same bootstrap procedure was also applied to a random dataset that peak by peak simulate the distribution of the actual data. Results from the actual data are compared against the ones from the simulated data to establish a statistically appropriate cutoff value on rank standard deviation for selecting peaks with consistent performance.

Example 1

Identification of Biomarkers that Detect Breast Cancer at the Early Stages

In order to identify potential biomarkers that can detect breast cancer at early stages, protein profiles of specimens from stages 0-I breast cancer patients were compared against those of the non-cancer controls. The analysis was performed in multiple iterations using all three modules in ProPeak. Through this iterative process the original full spectrum was reduced to a small subset of mass peaks that had consistently demonstrated a high level of significance in the optimal separation between the two selected diagnostic groups.

Once a small panel of biomarkers was selected, their ability to detect breast cancer was independently tested using data from stages II and III cancer patients. Based on the entire data set, a composite index was derived using multivariate logistic regression. Descriptive statistics including p-values from two-sample t-tests were estimated. Receiver-operating characteristic BLOC) curve analysis was then performed on the selected biomarkers and the composite index. Performance criteria such as sensitivities and specificities of the composite index were estimated using a bootstrap procedure. Efron B and Tibshirani R. Bootstrap Methods for Standard Errors, Confidence Intervals, and Other Measures of Statistical Accuracy. Statistical Science. 1986; 1:54-75. In this procedure, the total patient data set was divided through random re-sampling into a training set to derive a composite index through logistic regression and a test set for computing sensitivities and specificities. This re-sampling process was repeated many times. The results from multiple runs were finally aggregated to form the bootstrap estimate of the sensitivities and specificities.

Example 2

Peak Detection and Data Preprocessing

Figure 3:
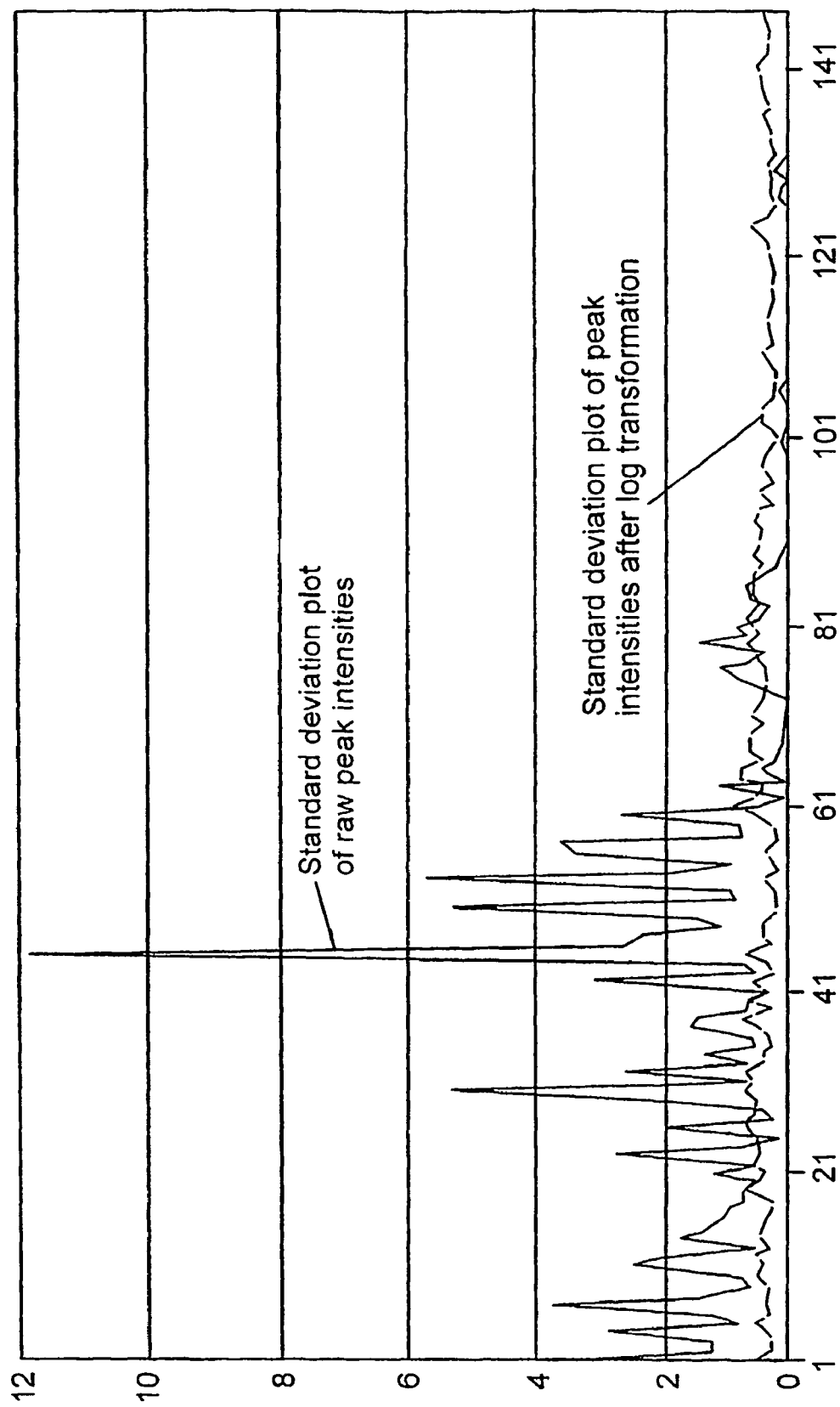
FIG. 3 shows the results of logarithmic transformation on data variance reduction and equalization.

Serum proteins retained on the IMAC-$Ni^{2+}$ chips were analyzed on a PBS-II mass reader. A total of 147 qualified mass peaks (S/N>5, cluster mass window at 0.3%) with M/Z over 2 KD were selected. Peaks of M'Z less than 2 KD are excluded to eliminate interference from the matrix. Mass accuracy of 0.1% was achieved by external calibration using All In 1 Protein Standard (Ciphergen Biosystems, Inc., CA). A representative spectrum obtained from such analysis is shown in FIG. 2. Logarithmic transformation was applied to the peak intensity values. The plots in FIG. 3 illustrate the effect of variance reduction and equalization through logarithmic transformation.

Example 3

Biomarker Selection Based on Early-Stage Cancer and Non-Cancer Controls

Figure 4B:
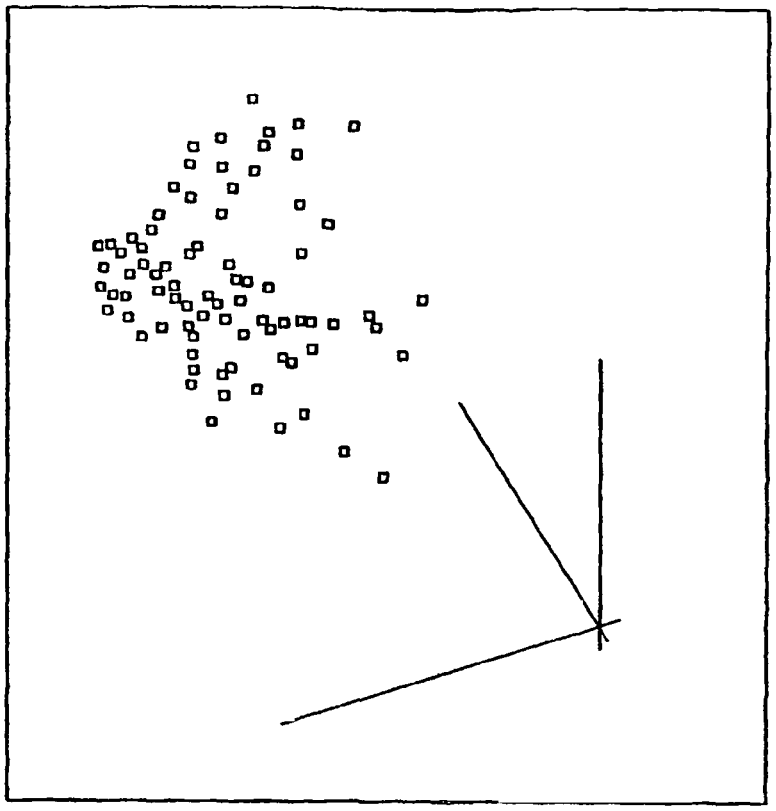
FIGS. 4A-4B show a 3 dimensional-UMSA-component plot of stages 0-I breast cancer (darker squares) versus non-cancer (white squares).
Figure 4A:
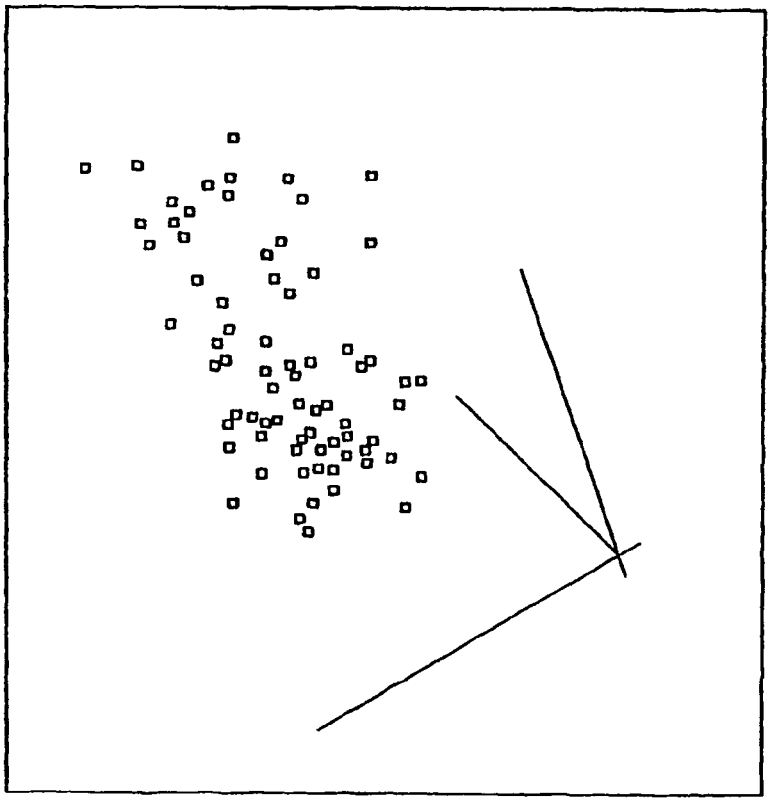
Figure 5:
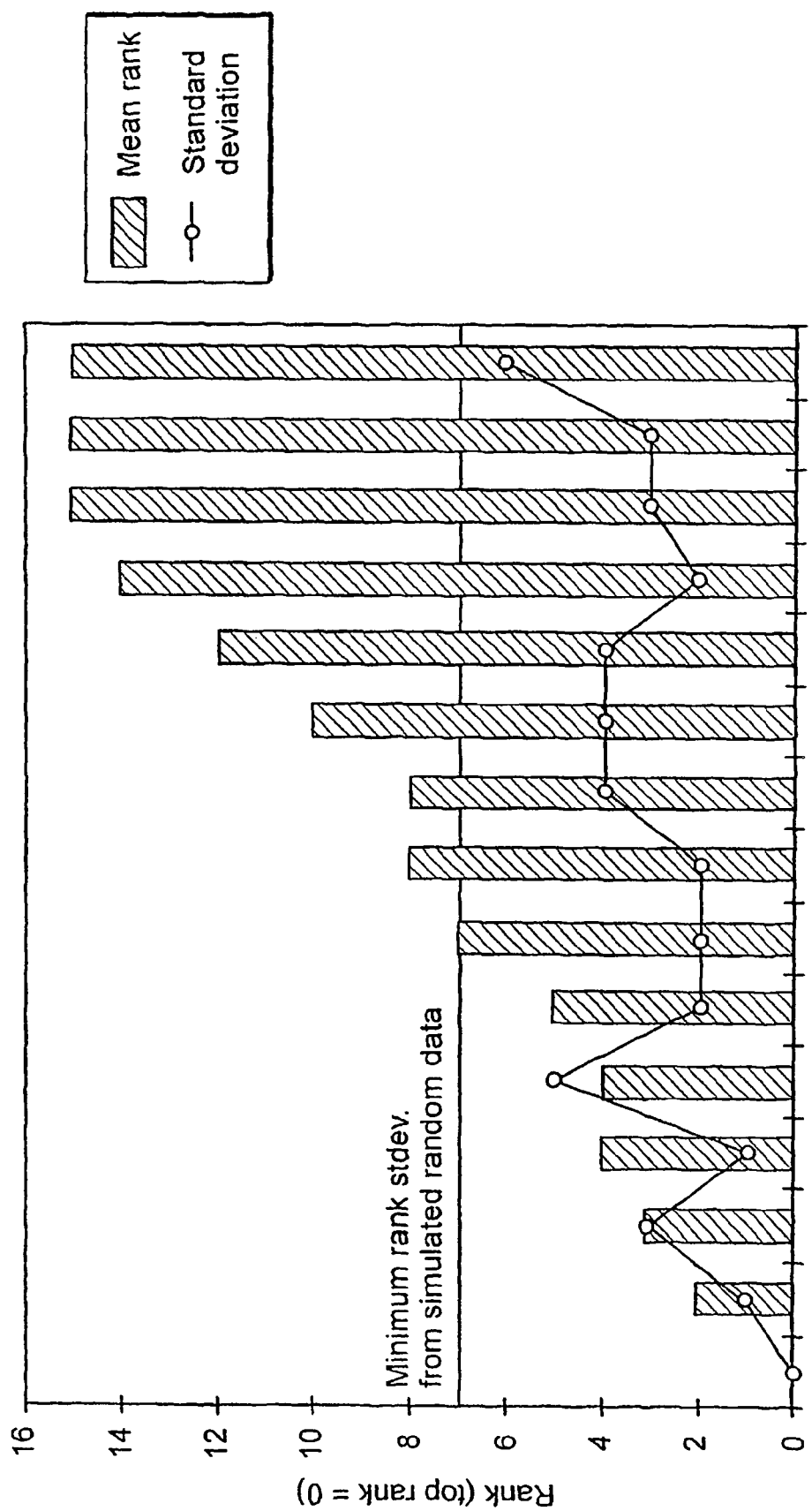
FIG. 5 is a graph showing fifteen peaks with top mean ranks and minimal rank standard deviations derived from ProPeak Bootstrap Analysis. Horizontal line at 7.0 was the minimum rank standard deviation computed by applying the same procedure to a randomly generated data set that simulated the distribution of the original data.

To identify biomarkers with potential for early detection of breast cancer, UMSA was performed using early-stage cancer as the positive group (Stage 0-4, n=42) and the non-cancer controls (HC+BN, n=66) as the negative group. Separability between the two groups was first tested using UMSA derived liner combination of all; 147 mass peaks. The early-stage cancer was separable from the non-cancer group when the entire protein profiles were compared. FIG. 4A plots the early-stage cancer (lighter) versus non-cancer (darker) in the UMSA component 3D space.

To select biomarkers that consistently perform well, UMSA were applied repeatedly for a total of 100 runs each with 30% leave out rate using the ProPeak BootStrap module. The same procedure was also applied to a simulated random data set. The minimal standard deviation derived from the simulated data was 7. In the experimental data, 15 mass peaks had standard deviation less then this value. This subset of mass peaks was selected as candidate biomarkers for further analysis. Their mean ranks and the corresponding standard deviations are plotted in FIG. 4.

Figure 6A:
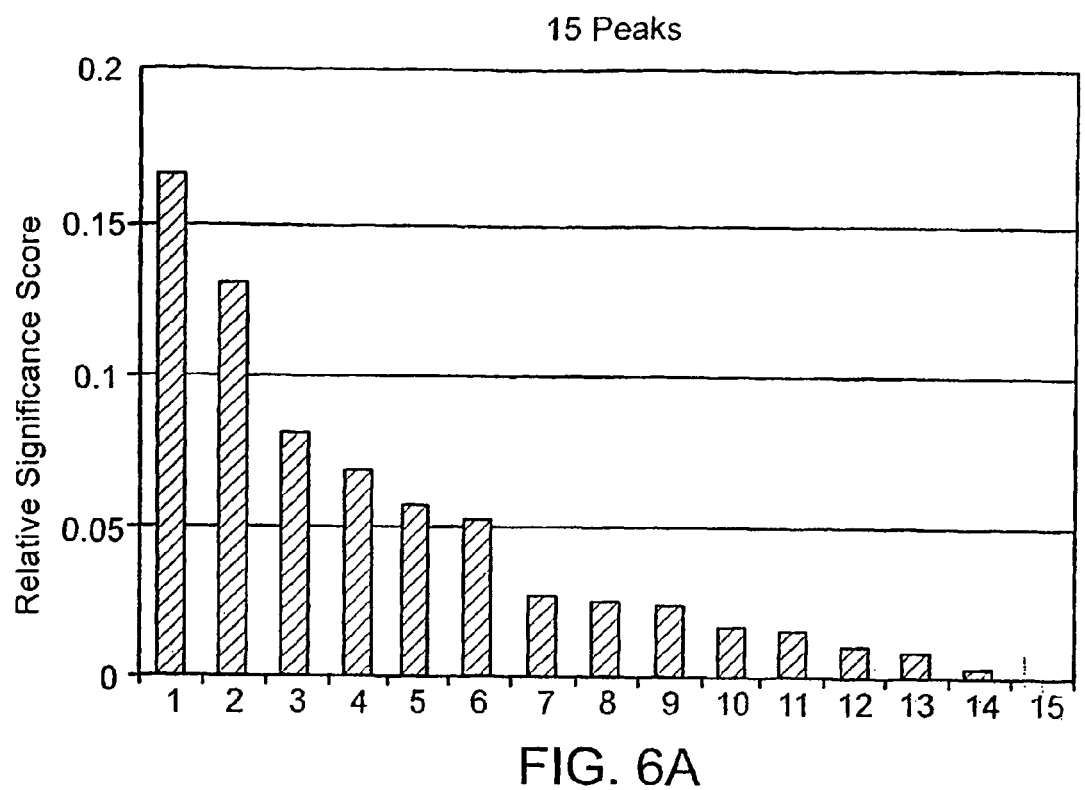
FIGS. 6A-6B are graphs showing a plot of absolute values of the relative significance scores of selected peaks based on contribution towards the separation between stages 0-I breast cancer and the non-cancer controls.
Figure 6B:
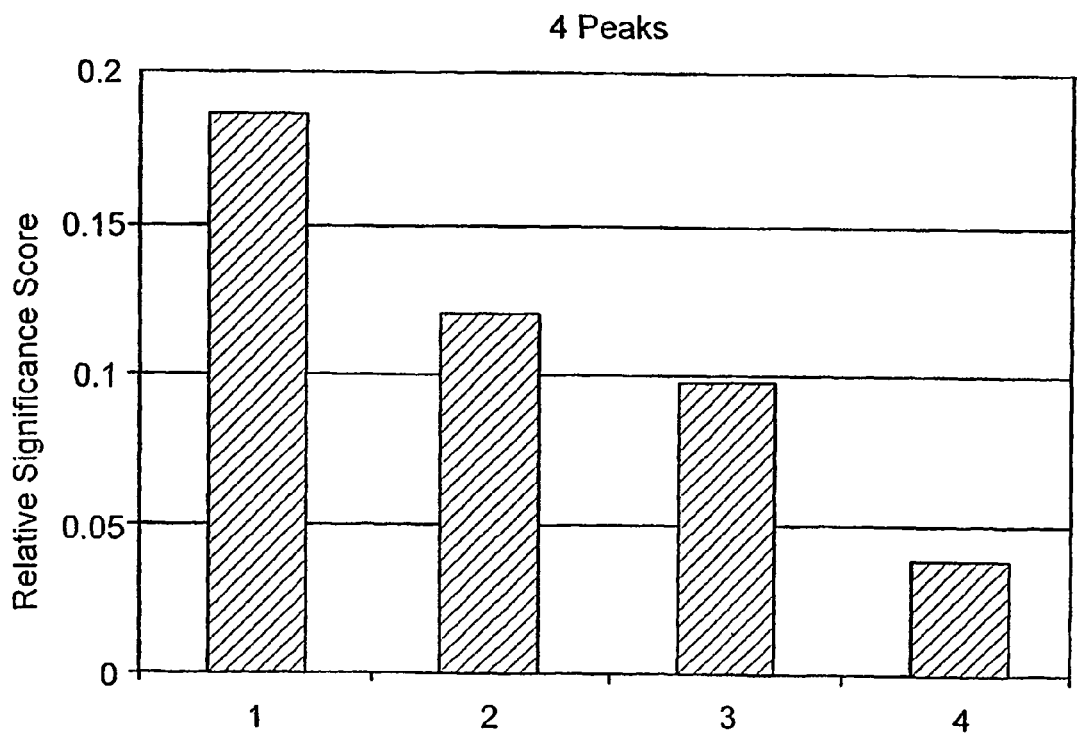
Figure 8A:
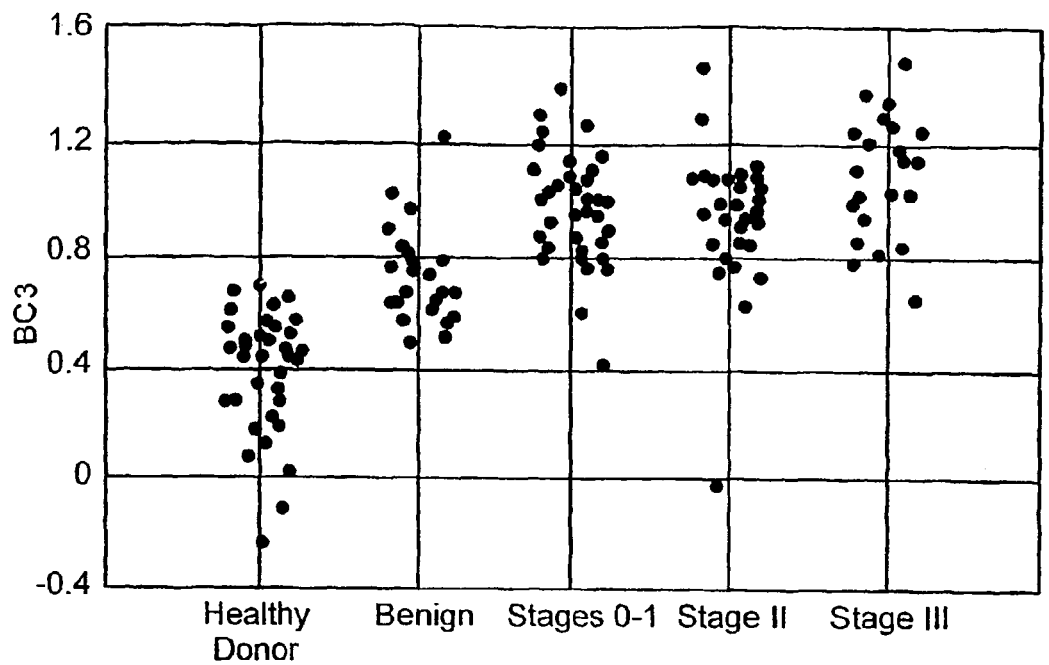
FIG. 8A-8B are scatter plots showing the distribution of the selected biomarker(s) across all diagnostic groups including clinical stages of the cancer patients.

To further rank the peaks in this reduced set of candidate biomarkers, the Stepwise Selection module of ProPeak was applied. The absolute value of the relative significance scores of the 15 peaks (see Table 5) are plotted in descending order in FIG. 8A, which shows that the majority of separability between the two groups of data was contributed by the first six peaks. Among these six peaks, four are unique. The other two were identified as doubly charged forms of the two of the unique peaks using ProteinChip Software 3.0. The recognition of both the doubly charged and the singly charged forms of the peaks suggests their importance in discriminating the selected two diagnostic groups. Taking away the doubly charged forms, the four unique peaks were recombined and evaluated using Stepwise Selection again. The recalculated relative significance scores are plotted in FIG. 6B. The top-scored three peaks, designated BC1, BC2, and BC3, were finally selected as the potential biomarkers for detection of breast cancer. BC1 appeared down regulated (scored negative) while BC2 and BC3 appeared up regulated (scored positive). A 3D-plot of stages 0-I breast cancer versus the non-cancer controls using these three biomarkers is shown in FIG. 4B.

Example 4

Evaluation of the Selected Biomarkers

Figure 7:
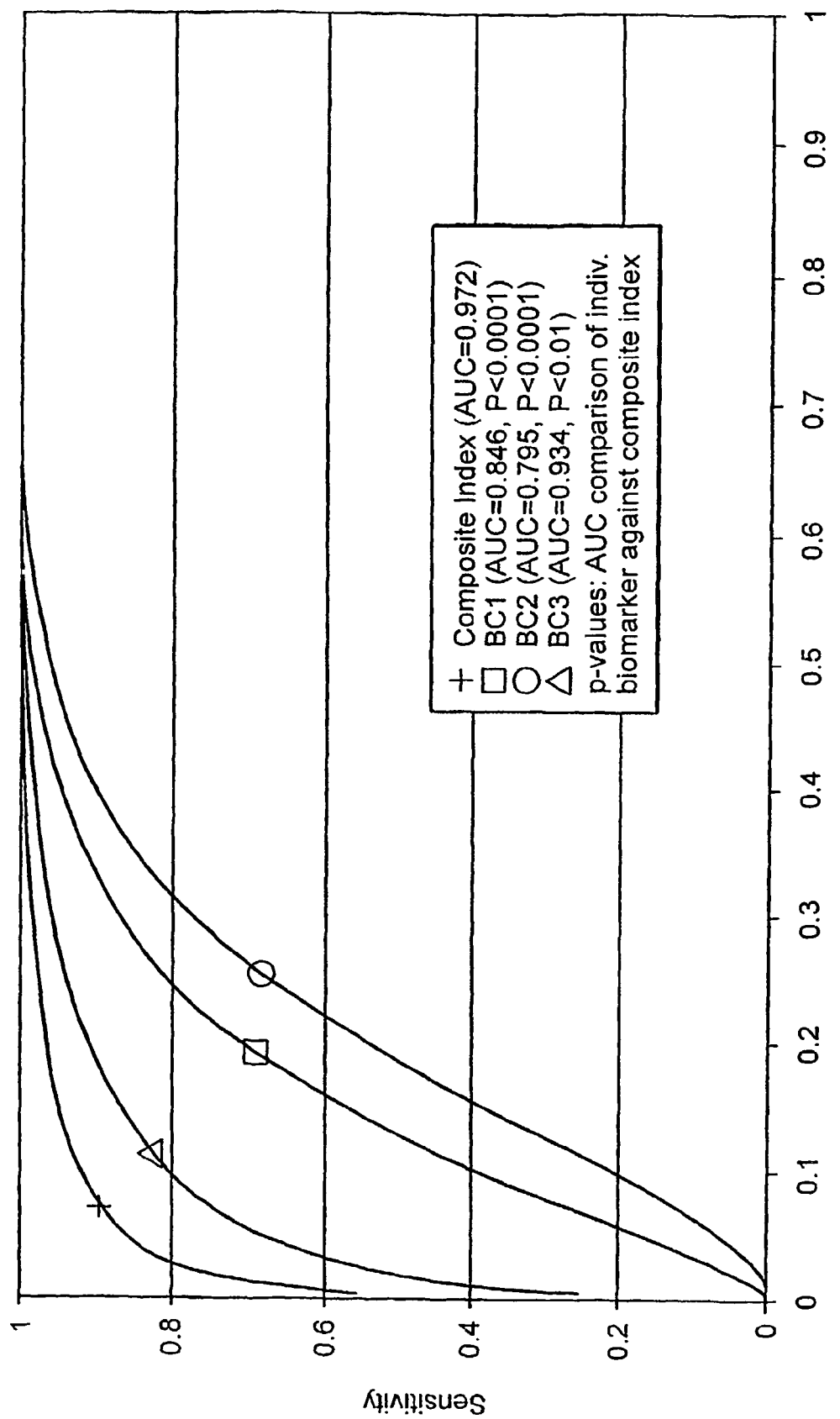
FIG. 7 is a graph showing receiver-operating-characteristic (ROC) curve analysis of BC1, BC2, BC3, and logistic regression derived composite index p-values from AUC (Area-under-curve) comparison between each individual biomarkers and the Composite Index are listed in the figure.

The descriptive statistics of these three biomarkers are listed in Table 2. FIG. 7 shows results from the ROC analysis. Among the three biomarkers, BC3 demonstrated the most individual diagnostic power. Its distributions over the diagnostic groups including clinical stages of cancer patients are plotted in FIG. 8A. The sensitivities and specificities of using BC3 alone at a cutoff value of 0.8 to differentiate the diagnostic groups are listed in Table 3A.

The estimated CV of the log transformed peak intensity was 6% for BC1, 7% for BC2, and 13% for BC3 (data not shown). Among the three biomarkers, BC3 had the largest CV of 13%. In comparison, the mean value of BC3 in the cancer patients was almost 90% above that in the non-cancer controls (calculated based on data in Table 2).

TABLE 2

Descriptive statistics of BC1, BC2, BC3, and the logistic regression derived composite index. Differences between non-cancer controls and stages 0-I, and between non-cancer controls and stages II-III, are both statistically significant ($p < 0.000001$) for all three biomarkers and the composite index.

|  | Non-cancer Controls (n = 66) | | Breast Cancer Patients Stages 0-I (n = 42) | | Breast Cancer Patients Stages II-III (n = 61) | |
| --- | --- | --- | --- | --- | --- | --- |
|  | Mean | Stdev | Mean | Stdev | Mean | Stdev |
| BC1 | 0.302 | 0.312 | −0.118 | 0.244 | −0.081 | 0.258 |
| BC2 | 0.981 | 0.358 | 1.411 | 0.154 | 1.295 | 0.205 |
| BC3 | 0.526 | 0.252 | 0.993 | 0.193 | 1.003 | 0.234 |
| Comp. Index | −0.375 | 0.313 | 0.425 | 0.257 | 0.349 | 0.242 |

Example 5

Combined Use of Three Selected Biomarkers

Figure 8B:
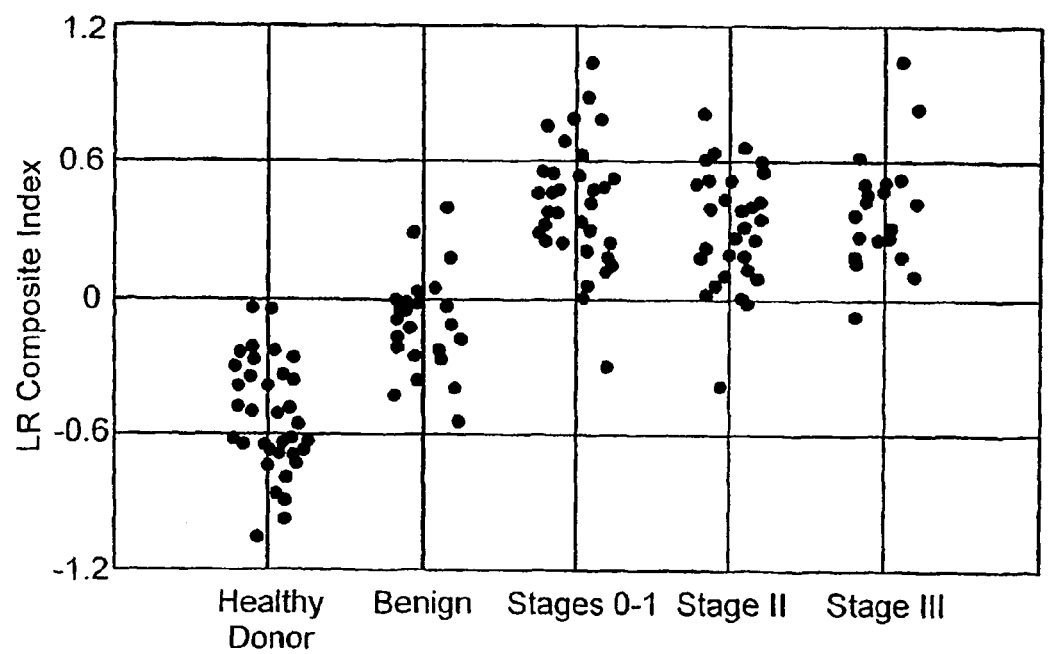
Figure 9:
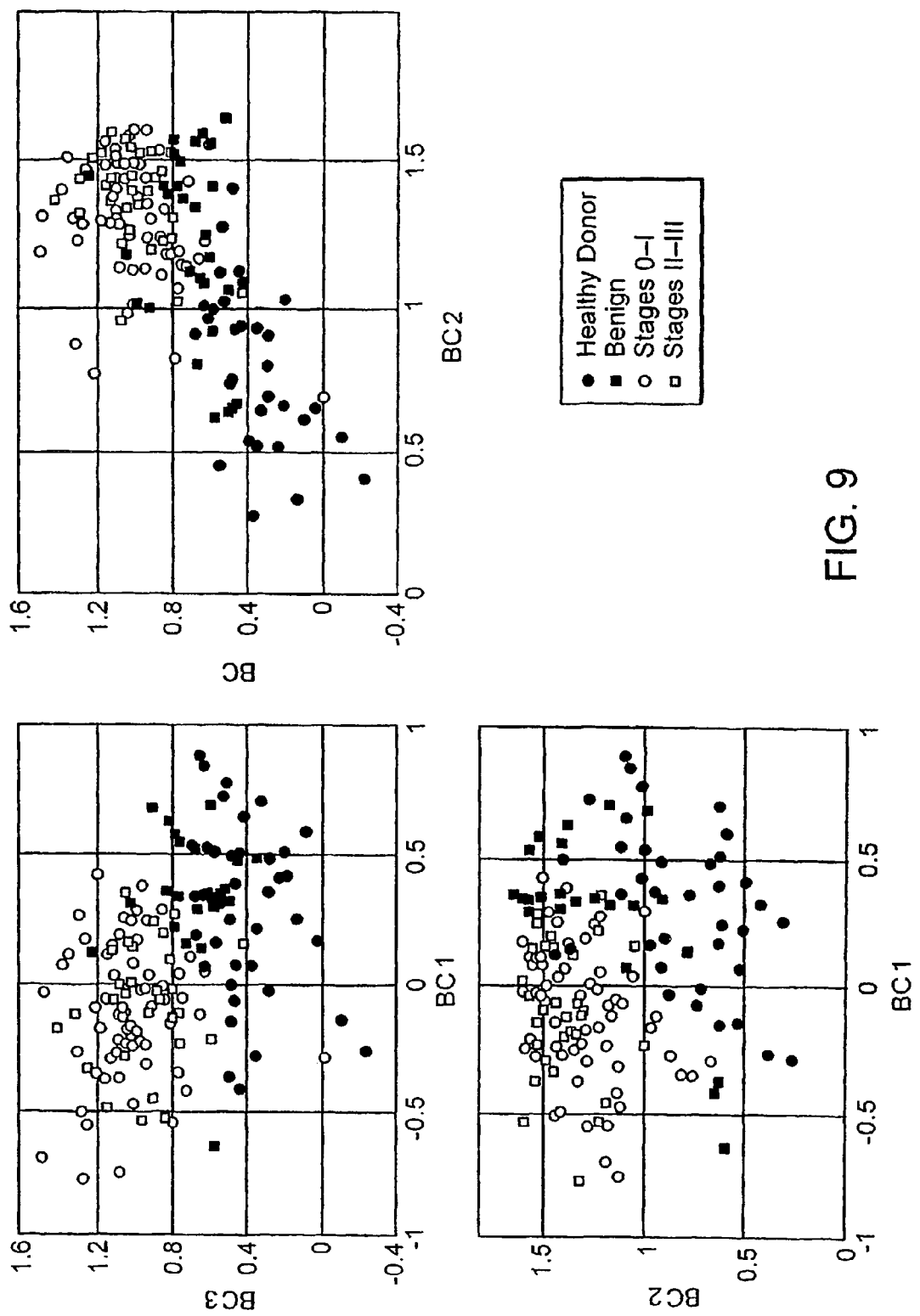
FIG. 9 shows a panel of three 2 dimensional scatter plots depicting distributions of all patient samples.

FIG. 9 compares the distribution of cancer patients at all clinical stages against non-cancer controls in all pair-wise biomarker combinations. Based on this observation, multivariate logistic regression was used to combine the three selected biomarkers to form a single-valued composite index. The descriptive statistics of this composite index are appended in Table 2. Its distributions over the various diagnostic group are plotted in FIG. 8B. ROC curve analysis of the composite index gave a much-improved AUC compared to the ones from individual biomarkers (FIG. 7).

Bootstrap cross-validation was used to estimate the diagnostic performance of the composite index (20 runs; in each run, 70% samples were randomly selected for composite index derivation and the remaining 30% for testing). The estimated sensitivities and specificities are listed in Table 3B.

The levels of the three potential biomarkers were also evaluated in relation to pT (tumor size) and pN (lymph node metastasis) categories. No significant correlation was observed.

TABLE 3A

Diagnostic performance of BC3.

| Cutoff = 0.8 | Non-Cancer Controls | | | Breast Cancer Patients Stage | | | |
| --- | --- | --- | --- | --- | --- | --- | --- |
|  | HC | Benign | Subtotal | 0-I | II | III | Subtotal |
| Negative | 0 41 (100%) | 6 19 (76%) | 6 60 (91%) | 37 (88%) 5 | 29 (78%) 8 | 22 (92%) 2 | 88 (85%) 15 |
| Total | 41 | 25 | 66 | 42 | 37 | 24 | 103 |

TABLE 3B

BootStrap estimated diagnostic performance of logistic
regression derived composite index using BC1, BC2
and BC3 (20 runs, leave out rate = 30%).

| LR at cutoff = 0 | Non-Cancer Controls | | | Breast Cancer Patients Stage | | | |
| --- | --- | --- | --- | --- | --- | --- | --- |
| | HC | Benign | Subtotal | 0-I | II | III | Subtotal |
| Negative | 100% | 85% | 91% (82-100%) | 93% | 85% | 94% | 93% (85-100%) |

Example 6

Detecting Breast Carcinoma In Situ by Serum Proteomic Analysis Using ProteinChip® Arrays and SELDI-Mass Spectrometry The protein profiles of 169 serum samples of women with and without breast cancer were analyzed, and a panel of three proteins (8.9 KD, 8.1 KD, 4.3 KD) were identified, that in combined use can detect breast cancer with high sensitivity (Stage 0-111, 93%) and specificity (Healthy Control+Benign, 91%). Among the three markers, the 8.9 KD protein performed the best. A sensitivity of 85%, and a specificity of 91% were achieved.

Ductal and Lobular Carcinoma In Situ (DCIS and LCIS) are the earliest forms (Stage 0) of non-invasive breast cancer. Nearly 100% of women diagnosed at this early stage of breast cancer can be cured. To validate these markers for early detection of breast cancer, the performance of the 3 previously identified biomarkers were evaluated using sera collected by a collaborating institution. The sample cohort consisted of 17 women with DCIS, 1 with LCIS, 8 with benign breast diseases, and 40 age-matched apparently healthy controls (45-65 years). Protein profiles were generated in triplicates using IMAC-Ni (Immobilized Metal Affinity Capture) ProteinChip arrays under the same experimental conditions as described supra. Log relative intensities of each of the three proteins were compared between different diagnostic groups using two-sample f-test. The expression patterns of two (8.9 KD and 8.1 KD) of the three markers were consistent with previous results. The p-values and the areas under the ROC curves of these two biomarkers are summarized in Table 4.

TABLE 4

Summary of Statistical Analysis

| | Two-sample t-test p-value | | Area under the ROC-curve | | Diagnostic performance | | |
| --- | --- | --- | --- | --- | --- | --- | --- |
| | DCIS/HC | DCIS/ HC + BN | DCIS/HC | DCIS/ HC + BN | Sensitivity (DCIS) | Specificity (HC) | Specificity (HC + BN) |
| 8.9 KD | 0.000059 | 0.000072 | 0.80 | 0.76 | 72% (13/18) | 65% (26/40) | 63% (30/48) |
| 8.1 KD | 0.0180 | 0.0194 | 0.76 | 0.71 | 61% (11/18) | 75% (30/40) | 75% (36/48) |

DCIS, Ductal Carcinoma In Situ; LCIS, Lobular Carcinoma In Situ; HC, Healthy Control; BN, Benign The following specific references also are incorporated by reference herein.

1. Jemal A, Thomas A, Murray T, Thun M. Cancer statistics, 2002. CA Cancer J Clin. 2002; 52:23-47.
2. National Cancer Institute. Cancer Net PDQ Cancer Information Summaries. Monographs on "Screening for breast cancer.", which document is available on the NIH website.
3. Antman K, Shea S. Screening mammography under age 50. JAMA. 1999; 281:1470-2.
4. Chan D W, Beveridge R A, Muss H, Fritsche H A, Hortobagyi G, Theriault R, et al. Use of Truquant B R Radioimmunoassay for early detection of breast cancer recurrence in patients with stage II and stage III disease, J Clin. Oncology. 1997; 15:2322-2328.
5. Karas M, Hillenkamp F. Laser desorption ionization of proteins with molecular masses exceeding 10,000 daltons. Anal Chem. 1988; 60:2299-2301.
6. Hutchens T W, Yip T T. New desorption strategies for the mass spectrometric analysis of micromolecules. Rapid Commun. Mass Spectrom. 1993; 7:576-80.
7. Merchant M, Weinberger S R. Recent advancements in surface-enhanced laser desorption/ionization-time of flight-mass spectrometry. Electrophoresis. 2000; 21:1164-67.
8. Wright Jr G L, Cazares L H, Leung S-M, Nasim S, Adam B-L, Yip T-T, et al. ProteinChip® surface enhanced laser desorption/ionization (SELDI) mass spectrometry: a novel protein biochip technology for detection of prostate cancer biomarkers in complex protein mixtures. Prostate Cancer Prostate Dis. 1999; 2:264-76.
9. Hlavaty J J, Partin A W, Kusinitz F, Shue M J, Stieg M, Bennett K, Briggman J V. Mass spectroscopy as a discovery tool for identifying serum markers for prostate cancer. Clin. Chem. [Abstract]. 2001; 47:1924-26.
10. Paweletz C P, Trock B, Pennanen M, Tsangaris T, Magnant C, Liotta L A, et al. Proteomic patterns of nipple aspirate fluids obtained by SELDI-TOF: potential for new biomarkers to aid in the diagnosis of breast cancer. Dis Markers. 2001; 17:301-7.
11. Vlahou A, Schellhanuner P F, Medrinos S, Patel K, Kondylis F I, Gong L, et al. Development of a novel proteomic approach for the detection of transitional cell carcinoma of the bladder in urine. Am J Pathol. 2001; 158: 1491-502.
12. Patricoin E F III, Ardekani A M, Hitt B A, Levine P J, Fusaro V A, Steinberg S M, et al. Use of proteomic patterns in serum to identify ovarian cancer. The Lancet. 2002; 359:572-577.
13. Zhang Z, Page G. Zhang H. Applying Classification Separability Analysis to Microarray Data, in Proc. of Critical Assessment of Techniques for Microarray Data Analysis (CAMDA'00), Kluwer Academic Publishers, 2001.
14. Vapnik V N, Statistical Learning Theory, John Wiley & Sons, Inc., New York, 1998.

15. Efron B and Tibshirani R. Bootstrap Methods for Standard Errors, Confidence Intervals, and Other Measures of Statistical Accuracy. Statistical Science. 1986; 1:54-75.

8.2. Example 7

Identification of Biomarkers BC-1, BC-2, and BC-3

Materials and Methods

Patient Samples

Archived serum samples from 176 women were chosen and analyzed retrospectively. These sera were collected from 2000 to 2002 by the National Cancer Institute of Italy and stored at −30° C. until use. All women provided informed consent prior to serum collection for this IRB (Internal Regulation Board) approved study. The cancer group included 32 cases of DCIS (36-80 yrs, mean=56 yrs) and 61 cases of invasive breast cancer (47 cases of ductal invasive, 9 cases of lobular invasive and 5 cases with mixed ductal and lobular features) (24-84 yrs, mean=56 yrs). Diagnoses were pathologically confirmed, and specimens were obtained before treatment. Additional clinical information for cancer patients includes ER/PR status, Elston grade, tumor size and lymph node status (invasive cases only). The controls included 37 women with various benign breast disease including 13 cases of atypical (18-77 yrs, mean=44 yrs), and 46 age-matched apparently healthy women (44-68 yrs, mean=52 yrs).

SELDI Protein Profiling

Protein profiles were generated using IMAC-Ni (Immobilized Metal Affinity Capture) chip arrays under the same binding and washing conditions as previously described. Briefly, we added 45 ml of 9M urea, 2% CHAPS, 50 mM Tris-HCl, pH 9 to 30 ml of each serum sample. The mixture was vortexed at 4° C. for 15 minutes and diluted 1:40 in phosphate buffered saline (PBS) pH 7.4. The IMAC3 chip arrays were activated with 50 mM $NiSO_4$ according to manufacturer's instructions (Ciphergen Biosystems, CA). 50 ml of diluted samples were applied to each spot on the ProteinChip Array by using a 96 well bioprocessor (Ciphergen Biosystems, CA). After binding at room temperature for 60 minutes on a platform shaker, the array was washed twice with 100 ml of PBS for 5 minutes followed by two quick rinses with 100 ml of $dH_2O$. After air-drying, 0.5 ml of saturated sinapinic acid (SPA) prepared in 50% acetonitrile, 0.5% trifluoroacetic acid was applied twice to each spot. All steps were automated using a Biomek-2000 workstation. The allocation of specimens on the chip arrays was randomized. Each specimen was processed and analyzed repeatedly in three independent experiments. Proteins bound to the chip surfaces were detected with a PBS-II ProteinChip Reader (Ciphergen Biosystems, CA). Data was collected by averaging 80 laser shots with an intensity of 240 and a detector sensitivity of 8.

Bioinformatics and Biostatistics

The data analysis process used in this study involved the following steps.

(a) Peak detection. ProteinChip Software 3.0 (Ciphergen Biosystems, CA) was used to collect and evaluate the raw spectra. Each set of 196 specimens including 176 study sera, 20 quality control sera (pooled human sera obtained from Serologicals Corp, GA) were compiled, baseline subtracted, and externally calibrated using All-In-1 Protein Standard (Ciphergen Biosystems, CA). Qualified mass peaks (visual examination) with mass-to-charge ratios (m/z) between 2K and 150K were manually selected. The peak intensities were normalized to the total ion current of m/z between 2.0 kD and 150 kD with the same external coefficient and the data were exported to an Excel spreadsheet.

(b) Evaluation of Reproducibility

The reproducibility of replicates was estimated by calculating the correlation of each pair of replicates and calculating the CV of the three reported peaks as calculated from pooled human sera. If no systemic bias observed, the peak intensities identified in replicate analysis were averaged and then log transformed.

(c) Marker Evaluation. Two sample t-test and Receiver-Operating-Characteristic (ROC) curve analysis (in house software implemented in MATLAB, version 6.0) analysis were performed for evaluation of the selected biomarkers.

Protein Identification

Protein purification was carried out according to individual biochemical properties using a series of protein separation procedures including anion exchange, size exclusion, and reverse phase chromatography, followed by SDS-PAGE separation. To monitor the purification process, healthy control samples were processed in parallel with the cancer samples. During each of the iterations, the new fractions were profiled on ProteinChip arrays to monitor the presence or absence of the biomarkers of interest. Gel band containing the targeted protein was identified by on chip analysis of the eluted protein, and digested with ASP-N. Peptide finger print was acquired on a PBSII ProteinChip reader. The masses of the proteolytic fragments were used for database searching with the ProFound algorithm. For confirmation, the NP20 arrays containing the proteolytic fragments were analyzed by collision-induced dissociation using a PE Sciex QStar (Concord, Canada) equipped with a ProteinChip Array interface (Ciphergen). Protein identification was carried out using the UCSF ProteinProspector MS-Tag program.

CA15-3

The value of CA 15-3 was determined using IRMA-mat CA 15-3 (Byk-Sangtec Diagnostica Dietzenbach—Germany).

Evaluation of BC-1, BC-2 and BC-3 by SELDI

A total of 71 peak clusters were manually selected in the 2 KD to 150 KD mass region. The reproducibility of three independent SELDI experiments was estimated using correlation analysis. The correlation coefficient (r) observed between the replicates is 0.885 (rep1 vs 2), 0.893 (rep 1 vs 3) and 0.865 (rep 2 vs 3). Since no systematic bias between pairs of replicates was identified, the averaged peak intensities at each M/Z value were used for further analysis. The estimated CVs of the log-transformed peak intensities for BC-1 (4.3 KD), BC-2 (8.1 KD) and BC-3 (8.9 KD) were 0.172, 0.117, and 0.156 respectively.

Figure 10:
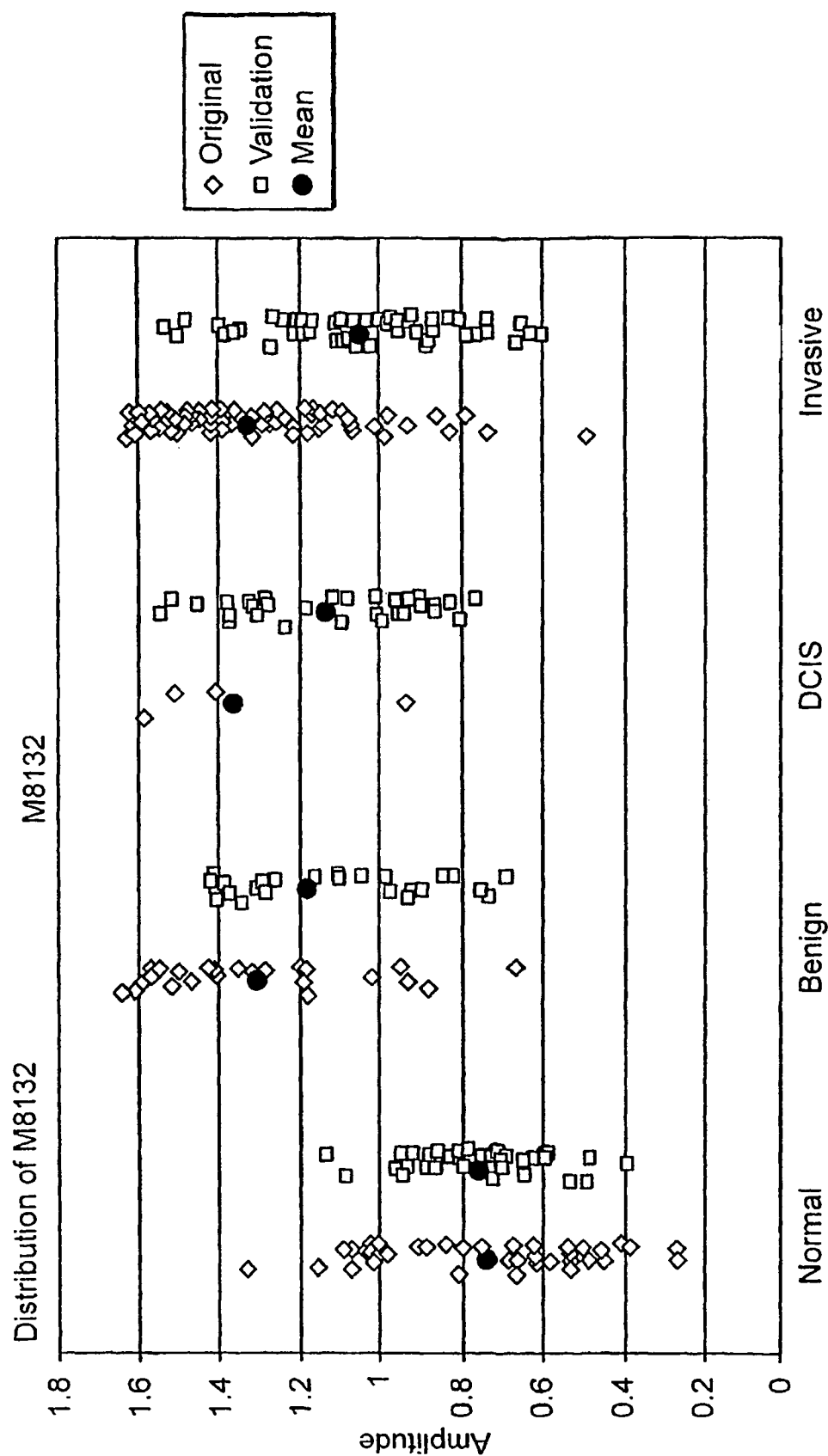
FIG. 10 shows the distribution of marker BC-2 (C3a-desArgΔ8).
Figure 11:
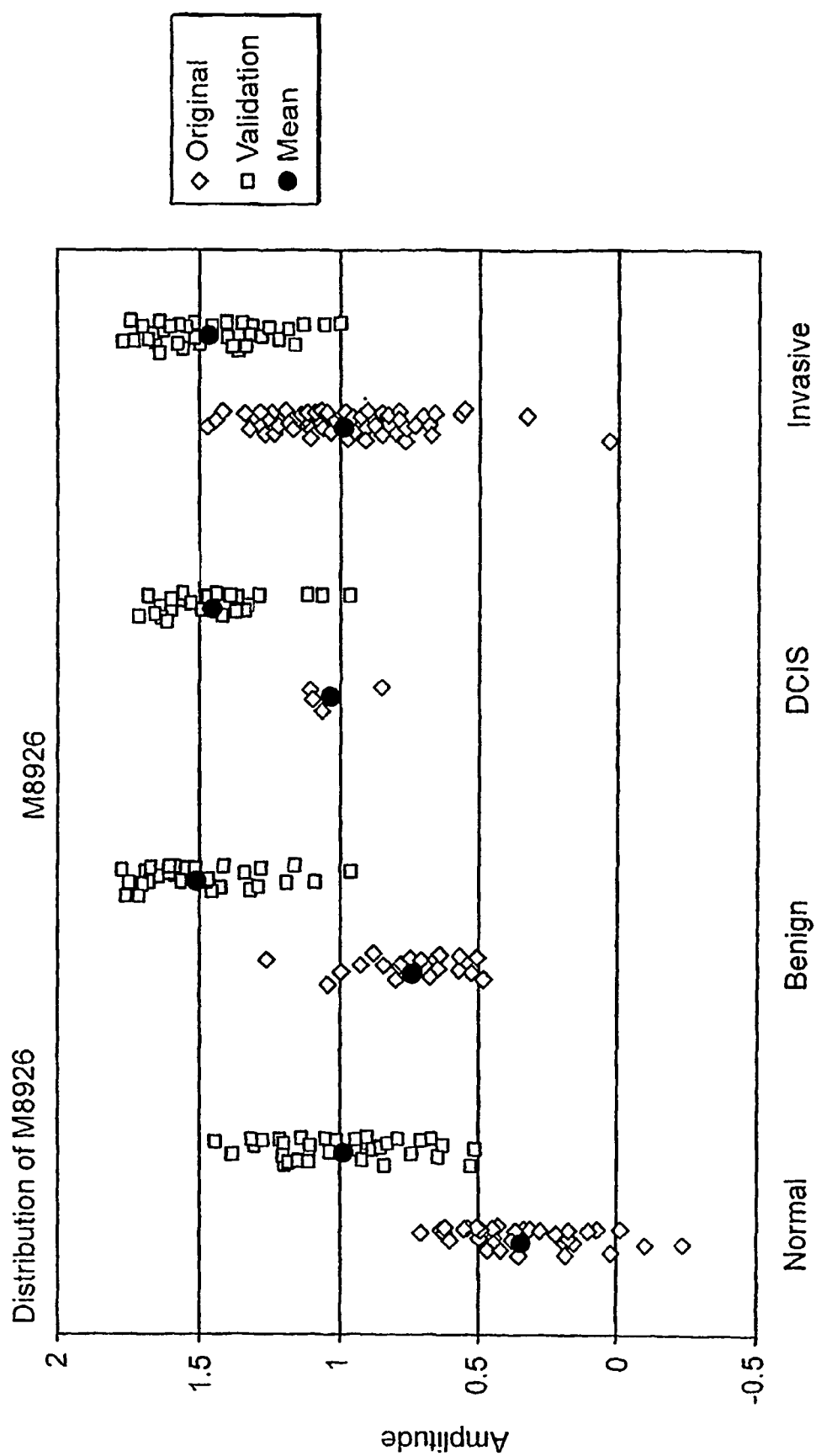
FIG. 11 shows the distribution of marker BC-3 (C3a-desArg).

For comparison purpose, distribution of BC-1, BC-2 and BC-3 in both data were displayed. Consistent with our previous results, levels of BC-2 and BC-3 were elevated in cancer, including DCIS (FIGS. 10 and 11). However, BC-1, which was found low in cancer previously, was elevated in cancer groups of the current data. Performance of BC-1 is unstable.

Example 3

Protein Identification

In parallel with the SELDI evaluation, we have determined the protein identity of the three markers.

BC-1, with m/z of 4.3 KD, was identified as a fragment of human inter-alpha trypsin inhibitor, heavy chain H4 (also referred to herein as "ITIH4", "IAIH4, or "PK-120").

BC-2, with m/z of 8.1 KD, is a truncated form of C3a-desArg (also referred to herein as C3a-desArg-8.1 or C3a-desArgΔ8). The amino acid sequence of C3a-desArgΔ8 is SVQLTEKRMDKVGKYPKELRKCCEDGM-RENPMRFSCQRRTRFISLGEACKKVFLDC CNYITEL-RRQHA (SEQ ID NO:2). This form has a theoretical mass of 8132 daltons, and the predicted pI is 9.38.

Figure 18:
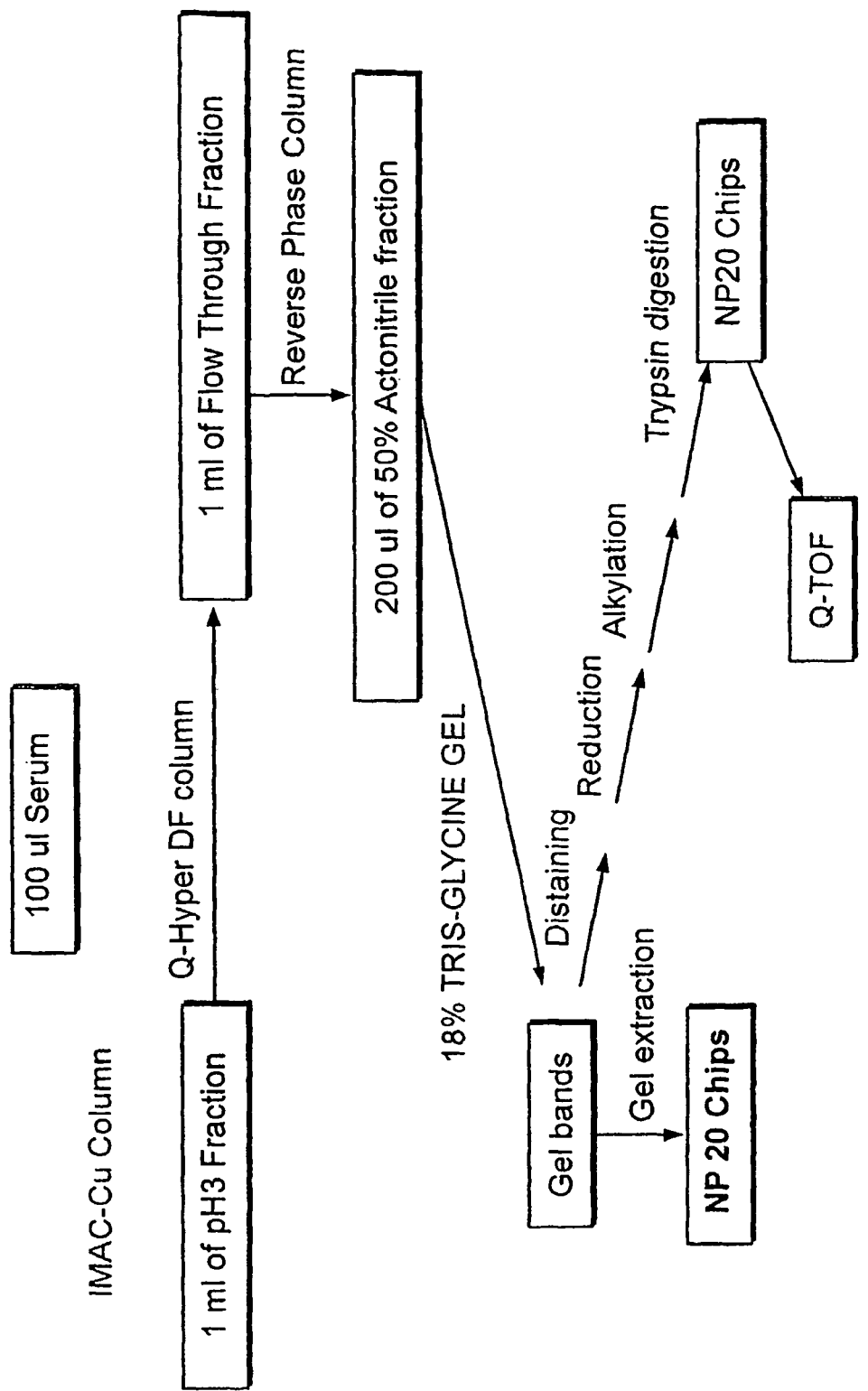
FIG. 18 shows the scheme used for purification and identification of marker BC-3.

BC-3, m/z of 8.9 KD, is identified as C3a-desArg. Procedure and result of protein identification is shown in FIGS. 18-19. The amino acid sequence of C3a-desArg is SVQLTEKRMDKVGKYPKELRKCCEDGM-RENPMRFSCQRRTRFISLGEACKKVFLDC CNYITEL-RRQHARASHLGLA, set forth as SEQ ID NO:1. Its predicted mass is 8923 daltons, consistent with the measured mass of 8926 daltons, and the predicted pI is 9.54, consistent with its inability to bind anion exchange resin at pH 9.0.

Figure 12:
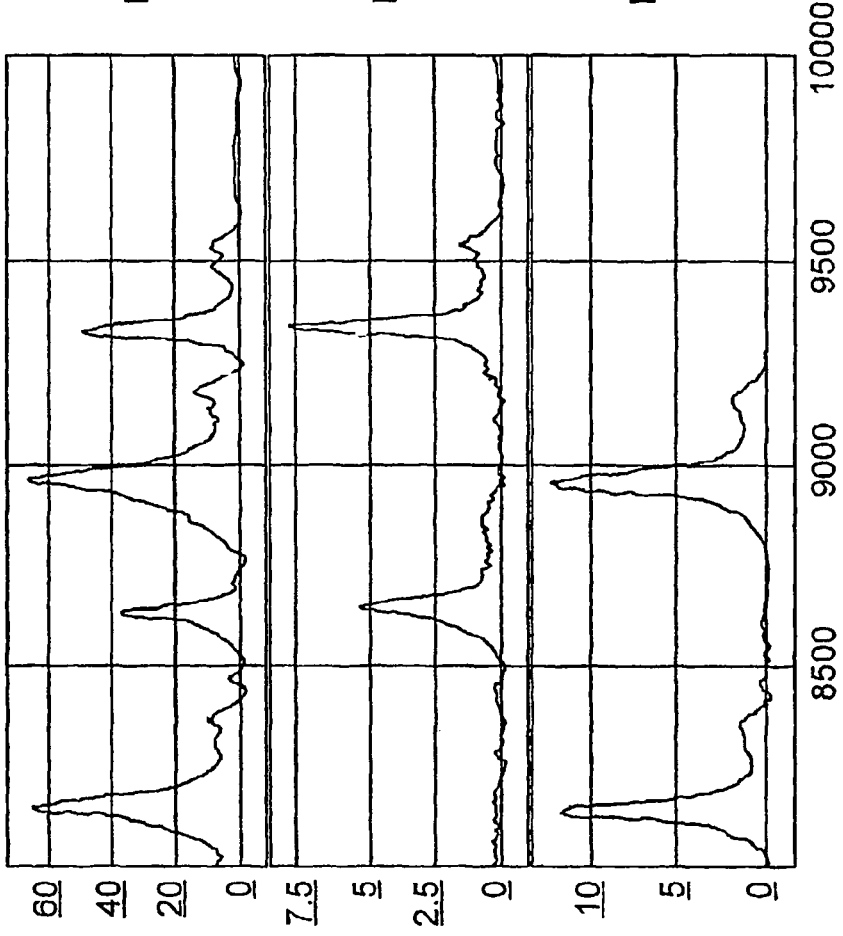

The identity of BC-2 and BC-3 was further verified by immuno-capture using mono-clonal antibody against C3a (FIG. 12). Similarly, BC-1 was captured antibody against ITIH4.

Independent Validation of BC-2 and BC-3 Using On-Chip Immunoassay

Figure 13:
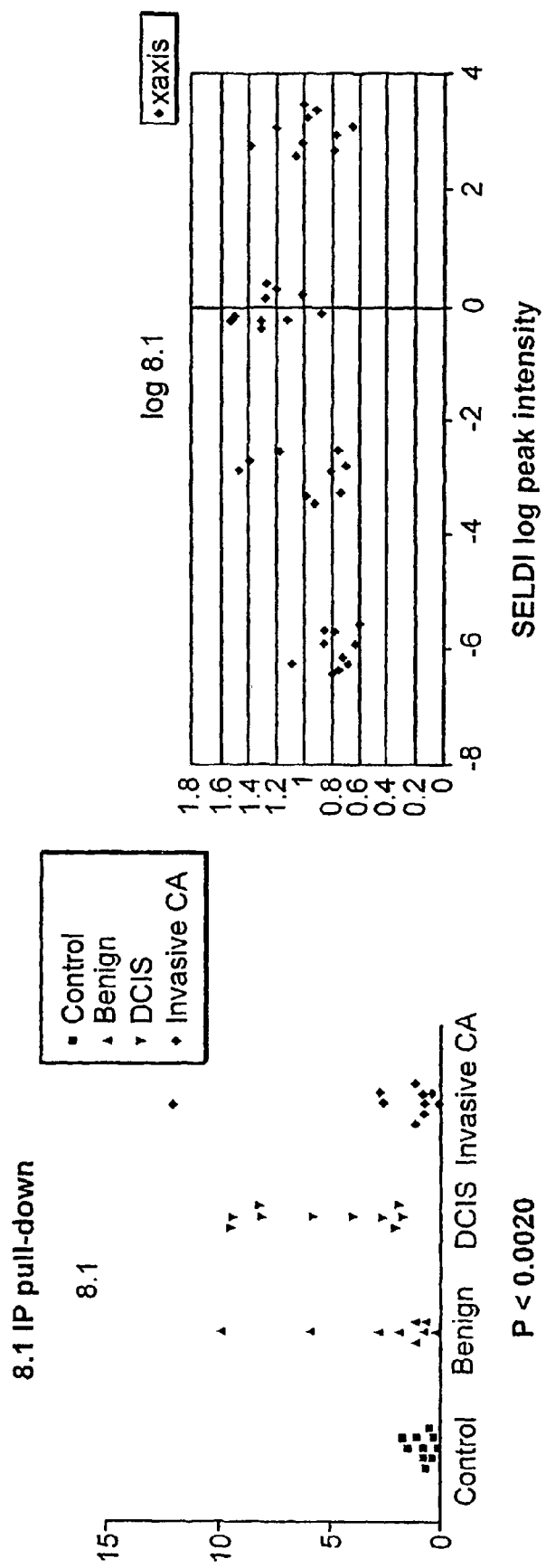
Figure 14:
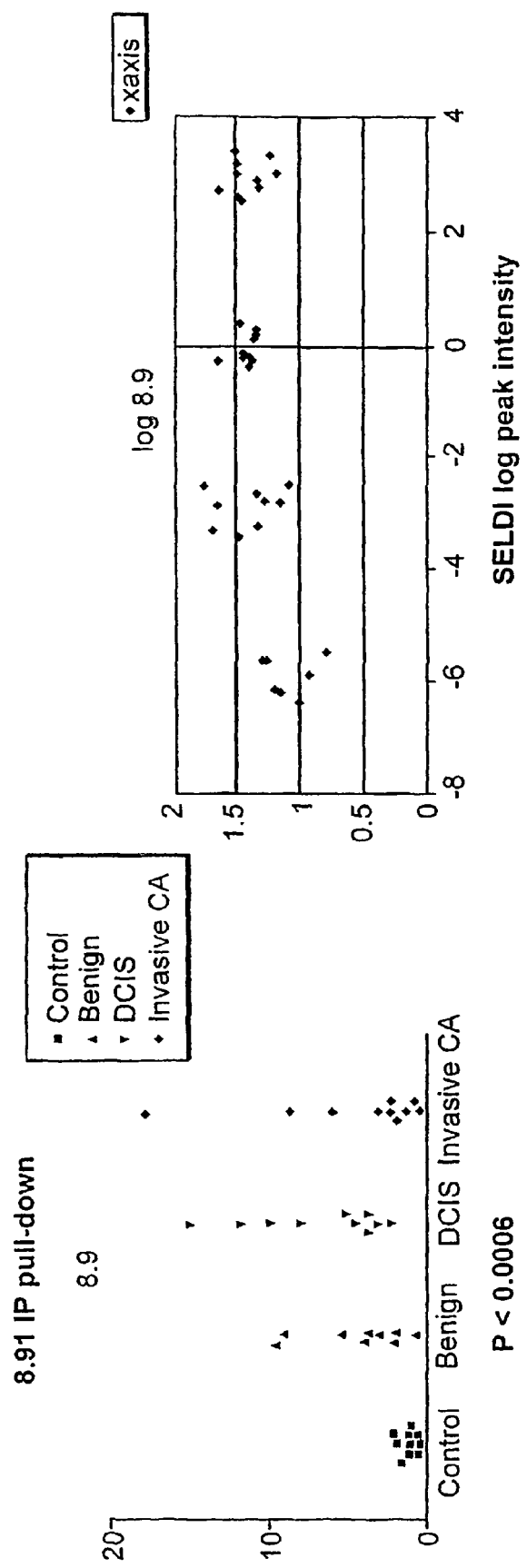

A small subgroup of the serum samples. (10 cases of normal, 9 cases of benign, 10 cases of DCIS and 10 cases of invasive) were randomly selected for an IP pull down experiment using antibody against C3a. Distribution of the captured C3a-desArg and C3a-desArg-8.1 in cancer and non-cancer groups is consistent with the SELDI result (FIGS. 13 and 14).

A 4.6 KD ITIH4 fragment (ITIH4 fragment 1b; BC-1b) is consistently down regulated in cancer in both cohorts ITIH4 is heavily processed, and several IHIH4 fragments were observed in serum. To investigate whether inconsistency on distribution of BC-1 is due to instability, we have also evaluated the distribution of full length ITIH4, and various processing products.

Figure 15:
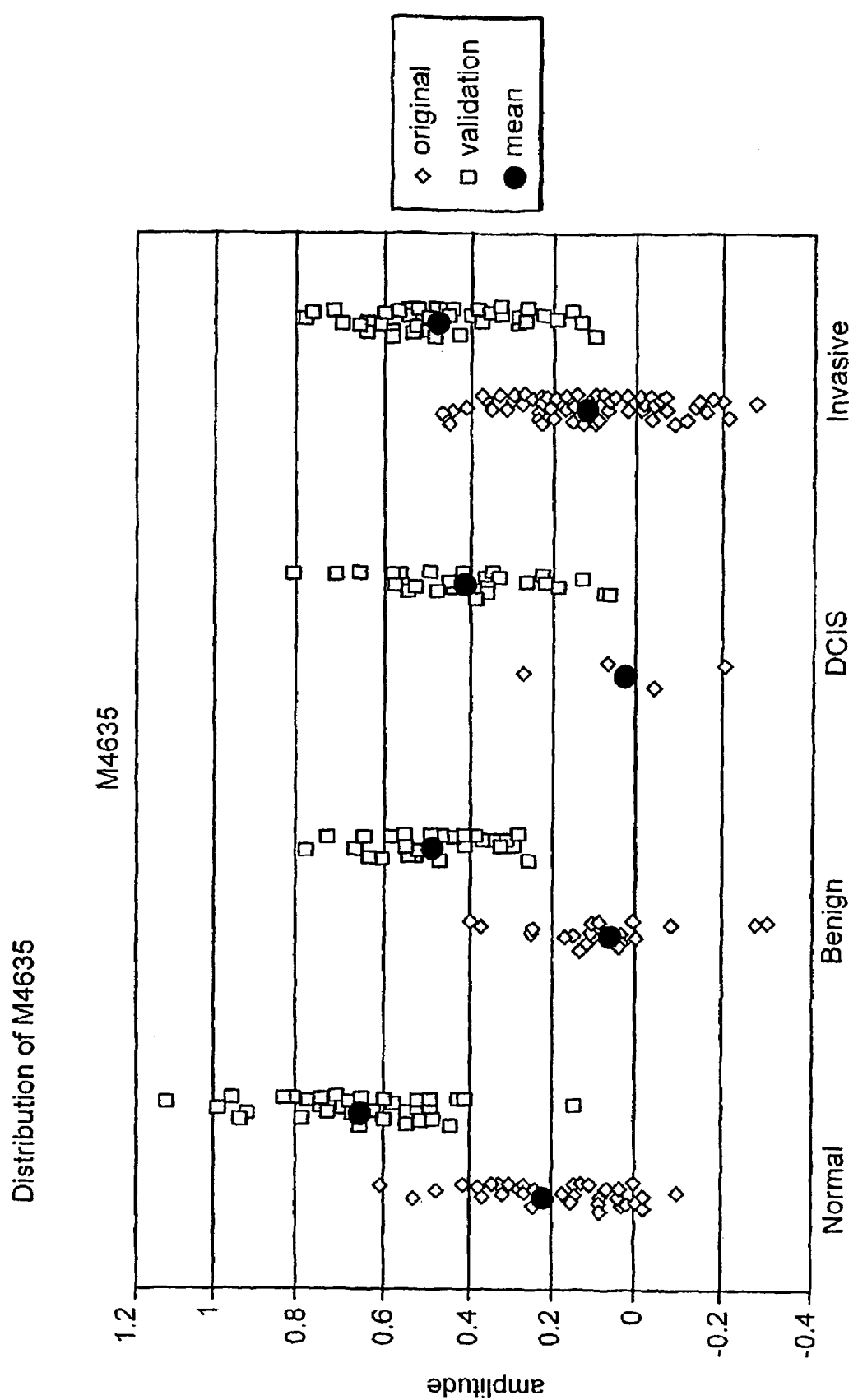
FIG. 15 shows the distribution of marker BC-1b (ITIH4 fragment 1b).
Figure 16:
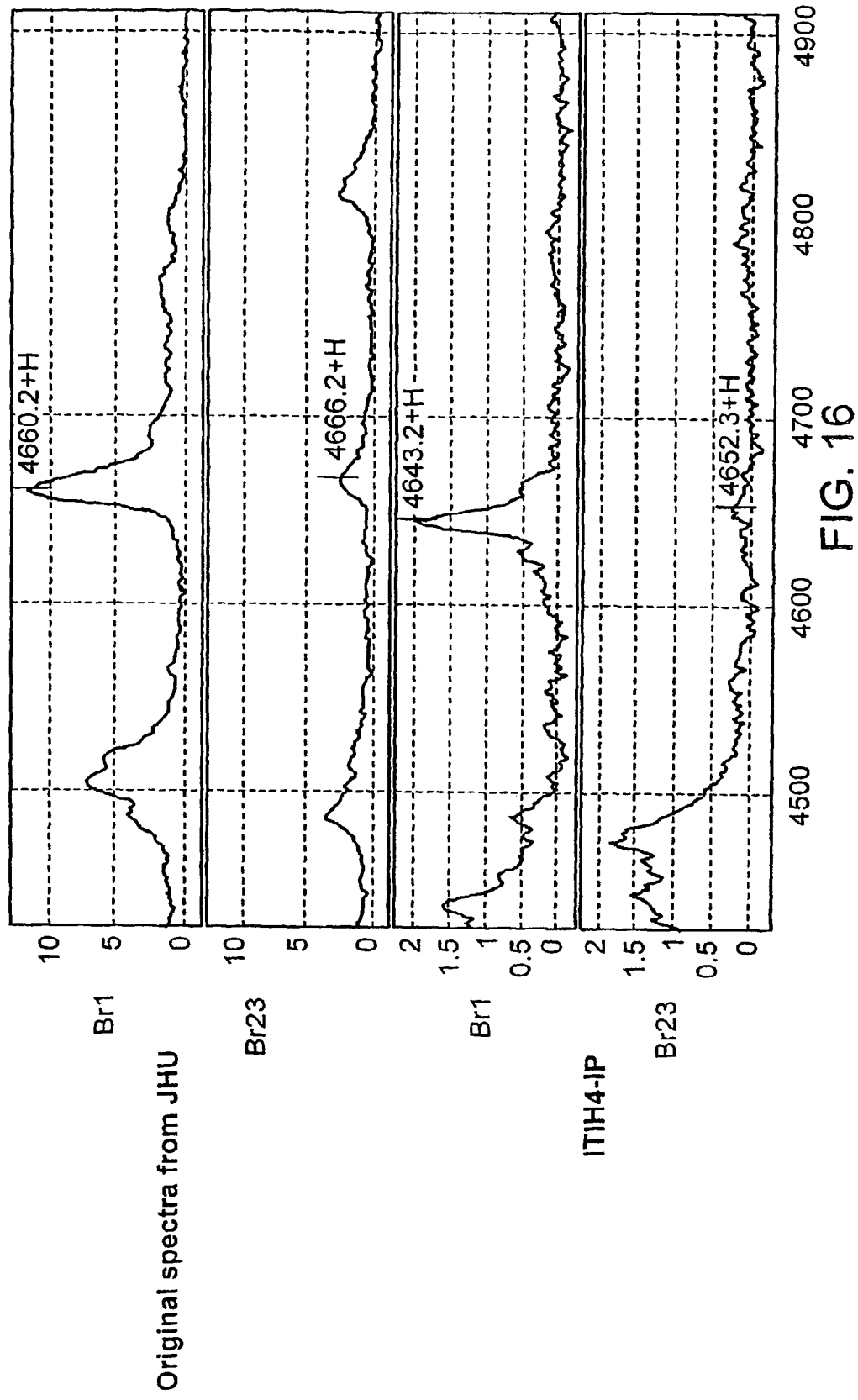
FIG. 16 shows the identification of various ITIH4 fragment in breast cancer samples.

A 4.6 KD fragment is found consistently down regulated in cancer in both cohorts, as shown in scatter plot in FIG. 15. Confirmation of the protein identity is shown in FIG. 16.

Diagnostic Performance of the Evaluated Biomarkers and CA15-3

Figure 17:
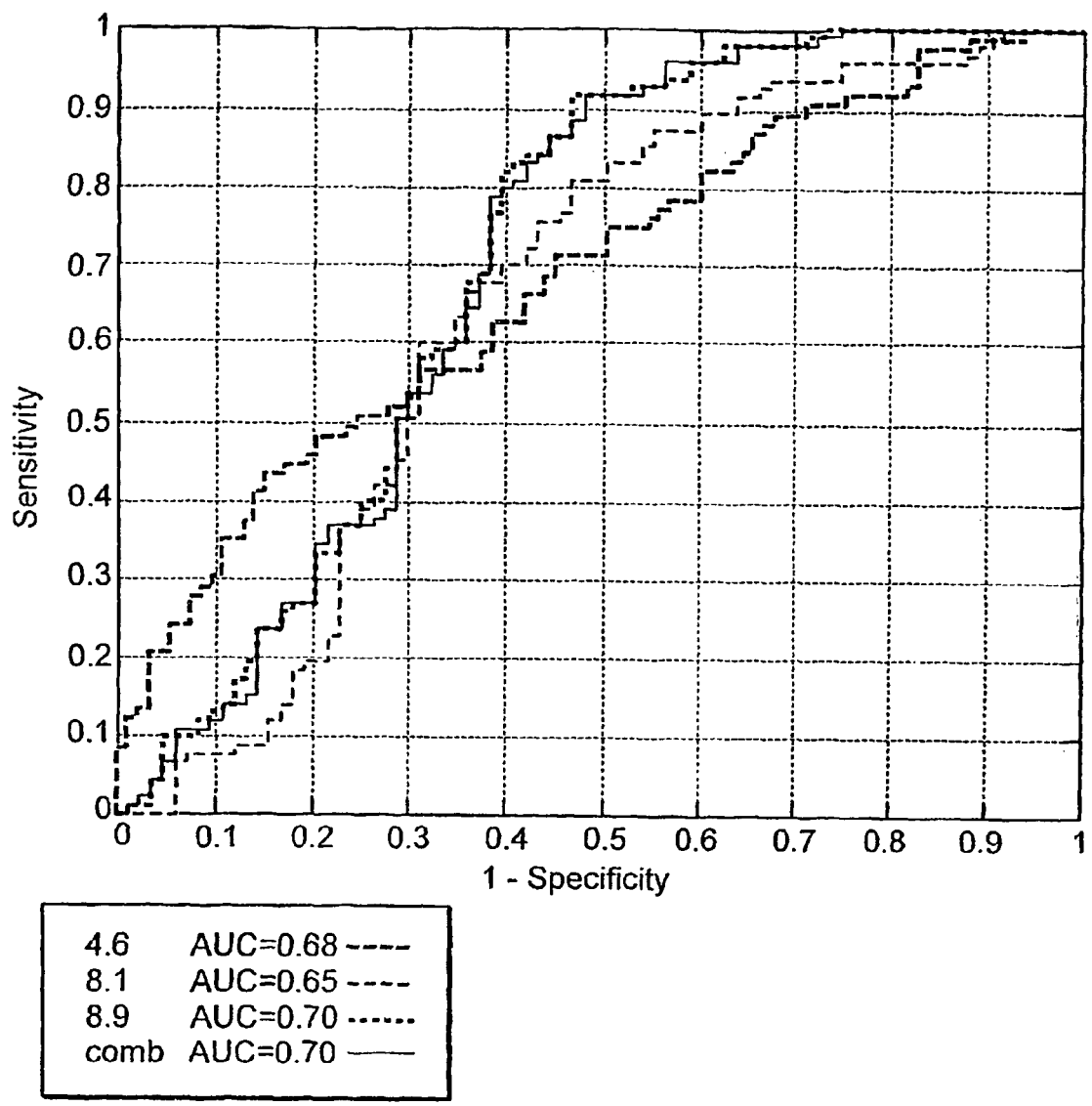
FIG. 17 shows the receiver operating characteristic (ROC) curve for markers BC-1b (ITIH4 fragment 1b), BC-2 (C3a-desArgΔ8), and BC-3 (C3a-desArg).

Although recommended only for monitoring therapy of advanced breast cancer or recurrence, CA115-3 and CA27.29 are the two primarily used serum tumor marker tests approved by the Food and Drug Administration for breast cancer {Chan DW, 2001 #46}. To investigate whether CA15-3 has any discriminatory power in this study cohort, we have measured the serum CA15-3 level using IRMA-mat CA 15-3 (Byk-Sangtec Diagnostica Dietzenbach—Germany). Of 176 study sera tested, only 5 (all from patients with invasive cancer) were tested positive using. 30 unit/ml cutoff. No significant difference was observed between healthy controls, benign, DCIS and invasive cancer groups (Data not shown). CA15-3 is ineffective in the detection of breast cancer. The diagnostic performance of the evaluated three biomarkers in terms of ROC analysis is presented in FIG. 17. Area under the curve for BC-2, BC3, 4.6 in the validation data is 0.65, 0.70, and 0.68, respectively.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Technological developments in high-throughput protein expression measurement have made it possible to compare proteomics expression patterns of clinical specimens on a large-scale. However, screening for new diagnostic markers that are truly associated with a particular disease process in the presence of large biological variability, as well as biases in data due to pre-analytical and analytical variables remains a challenging task.

In a previous study, we have analyzed protein profiles of 169 serum samples of patients with or without breast cancer using SELDI and ProteinChip arrays. Protein/peptide that bad significant contribution towards the optimal separation of the cancer and non-cancer cohort was selected using ProPeak, an in house software package developed for analysis of DNA array and Protein array data {Zhang, 2001 #176}. To avoid the selection of false markers whose high discriminatory power is purely by chance due to artifacts in the data that are unrelated to the disease process, several steps were taken in our data analysis. First, ProPeak BootStrap module introduced random perturbations in multiple runs and used the averaged peak rank to give a more reliable estimation of the peaks discriminatory power {Efron, 1986 #178}. Second, in order to establish an upper bound cutoff value on a peak's rank standard deviation for its performance not to be considered as purely by chance, the same bootstrap procedure was applied to a randomly generated data set that simulates the distribution of the real data. The minimum value of rank standard deviations from such "simulated peaks" indicates the level of consistency that a peak might achieve by random chance. This minimum value was used as the cutoff to reduce the original 147 peaks to a subset of 15 top-ranked peaks whose performance should be less likely due to random artifacts within the data. The 3 most significant discriminators, BC-1, BC-2 and BC-3 were further selected within this reduced set of peaks using backward stepwise selection. Although we have taken several steps to minimize the selection of false marker due to analytical variables, the validity of the three markers are limited since the study did not have a complete independent test set. The discriminatory power of the selected makers may still be associated with a certain preanalytical bias such as differences in collection procedure or storage conditions of different diagnostic groups. To address this issue, and to evaluate these markers for the detection of the earliest form of breast cancer, we tested these markers using DCIS sera collected independently by a collaborating institution. Although we can not rule out the possibility that the same preanalytical bias is present in both data, but the chance should be much lower.

In summary, we have evaluated the performance of 3 serum biomarkers for breast cancer early detection using sera collected by an independent source. Although several panel of biomarkers have been reported for various diseases using SELDI and ProteinChip arrays {Adam, 2002 #171; Adam, 2003 #22; Clarke, 2003 #1-16; Koopmann, 2004 #78; Li, 2002 #137; Paweletz, 2001 #36; Petricoin, 2002 #170; Rosty, 2002 #143; Vlahou, 2003 #48; Vlahou, 2001 #174; Vlahou, 2003 #90} {Li, 2004 #346}, this is so far the first validation study reported using independent test set. Whereas current serum tumor markers approved for breast cancer such as CA15-3 remains ineffective in breast cancer early detection, this panel Of biomarkers has a potential for discriminating the early stage breast cancer (DCIS) versus the healthy controls.

What is claimed is:

1. A method for diagnosing breast cancer in a subject comprising:
   (a) measuring biomarkers human inter alpha trypsin inhibitor heavy chain H4 (ITIH4) fragment 1b (BC-1b), and either C3a-desArgΔ8 (BC-2) or C3a-desArg (BC-3) in serum from the subject with mass spectrometry; and
   (b) comparing the measured level of ITIH4 fragment 1b (BC-1b) to a normal control level, and comparing the measured level of C3a-desArgΔ8 (BC-2) or C3a-desArg (BC-3) to a non-cancer control, wherein detection of a reduced level of ITIH4 fragment 1b (BC1-b), and an increased level of either C3a-desArgΔ8 (BC-2) or C3a-desArg (BC-3) correlates with breast cancer, and failure to detect a reduced level of ITIH4 fragment 1b and an increased level of C3a-desArgΔ8 (BC-2) or C3a-desArg (BC-3) correlates with non-breast cancer, wherein the ITIH4 fragment 1b (BC1-b) has an m/z of about 4.6 kD and the C3a-desArgΔ8 (BC-2) consists of SEQ ID NO:2 and the C3a-desArg (BC-3) consists of SEQ ID NO:1.

2. The method of claim 1, comprising measuring in serum of the subject with mass spectrometry: ITIH4 fragment 1 (BC-1), C3a-desArgΔ8 (BC-2), and C3a-desArg (BC-3), wherein ITIH4 fragment 1 (BC-1) has an m/z of about 4.3 kD.

3. The method of claim 2 further comprising measuring CA15-3 in the serum.

4. The method of claim 1, wherein said biomarkers are measured by capturing the biomarkers on an adsorbent surface of a SELDI probe and detecting the captured biomarkers by laser desorption-ionization mass spectrometry.

5. The method of claim 1, wherein the correlating is performed by a software classification algorithm.

6. The method of claim 1, wherein breast cancer is selected from non-invasive breast cancer and invasive breast cancer.

7. The method of claim 1, further comprising: (c) managing subject treatment based on the diagnosis.

8. The method of claim 4, wherein the adsorbent is a IMAC-Ni adsorbent.

9. The method of claim 4, wherein the adsorbent is a biospecific adsorbent.

10. The method of claim 9, wherein the biospecific adsorbent comprises an antibody.

11. The method of claim 7, wherein, if the measurement correlates with breast cancer, then managing subject treatment comprises administering a chemotherapeutic agent or radiation to the subject.

12. The method of claim 7, further comprising: (d) measuring said biomarkers after subject management and correlating the measurement with disease progression.

* * * * *